US007001608B2

(12) United States Patent
Fishman et al.

(10) Patent No.: US 7,001,608 B2
(45) Date of Patent: *Feb. 21, 2006

(54) ARTIFICIAL SYNAPSE CHIP INTERFACE FOR ELECTRONIC PROSTHETIC RETINA

(75) Inventors: Harvey A. Fishman, Menlo Park, CA (US); Mark Blumenkranz, Portola Valley, CA (US); Stacey F. Bent, Palo Alto, CA (US); David M. Bloom, Wilson, WY (US); Mark C. Peterman, Stanford, CA (US)

(73) Assignee: The Board of Trustees of the Lealand Stanford Junior University, Palo Alto, CA (US)

( * ) Notice: Subject to any disclaimer, the term of this patent is extended or adjusted under 35 U.S.C. 154(b) by 326 days.

This patent is subject to a terminal disclaimer.

(21) Appl. No.: 10/184,210

(22) Filed: Jun. 27, 2002

(65) Prior Publication Data
US 2003/0032946 A1     Feb. 13, 2003

Related U.S. Application Data

(60) Provisional application No. 60/301,934, filed on Jun. 29, 2001.

(51) Int. Cl.
*A61F 2/14* (2006.01)

(52) U.S. Cl. .................. 424/427; 623/4.1; 623/6.63; 623/24; 623/25; 623/26; 435/325; 435/395; 424/422

(58) Field of Classification Search ............. 623/4.1, 623/6.63, 24, 25, 26; 435/325, 375, 366, 435/395; 606/152; 424/422, 427
See application file for complete search history.

(56) References Cited

U.S. PATENT DOCUMENTS

| 5,962,027 A | 10/1999 | Hughes |
| 6,045,791 A | 4/2000 | Liu |
| 6,676,675 B1 * | 1/2004 | Mallapragada et al. ..... 606/152 |
| 2003/0104614 A1 * | 6/2003 | Uhrich et al. ............... 435/325 |

FOREIGN PATENT DOCUMENTS

| WO | WO 98/22819 | 5/1998 |
| WO | WO 01/81552 | 11/2001 |

OTHER PUBLICATIONS

"Circuit" Merriam-Webster Online Dictionary http://www.m-w.com/cgi-bin/dictionary?book=Dictionary&va=circuit accessed Feb. 14, 2005.*

(Continued)

*Primary Examiner*—Leon B. Lankford, Jr.
*Assistant Examiner*—Allison M. Ford
(74) *Attorney, Agent, or Firm*—Lumen Intellectual Property Services, Inc.

(57) ABSTRACT

The invention provides microfabricated devices and methods for directing the growth of a cell process to form an artificial synapse. The devices are called artificial synapse chips. The artificial synapse comprises a nanofabricated aperture (about 50–100 nm in size) that connects the cell process to a chemical or electrical means of neuronal excitation. Such an aperture width mimics the length scales of a natural synapse and thus emphasizes the localized spatial relationship between a neuron and a stimulation source. The invention further provides devices and methods for regenerating a nerve fiber into an electrode. The invention thus provides a regeneration electrode that uses a novel neural interface for stimulation and that uses novel surface methods for directing neuronal growth making possible in vivo connection of the devices to neural circuitry in a retina and other anatomical locations.

10 Claims, 12 Drawing Sheets

OTHER PUBLICATIONS

Chow et al, IEEE Transactions on Neural Systems and Rehabilitation Engineering, Mar. 2001, vol. 9, No. 1, pp. 86-95.*

Fishman et al, ARVO Annual Meeting Abstract Search and Program Planner, Abstract No. 2846, vol. 2002 from Annual Meeting of the Association For Research in Vision and Ophthalmology, Ft. Lauderdale, FL, May 5-10, 2002.*

Bernard, Andre et al. "Printing Patterns of Proteins" (1998) Langmuir, vol. 14, No. 9, pp. 2225-2229.*

L. Lu et al., "Retinal pigment epithelium cell culture on thin biodegradable poly(DL-lactic-co-glycolic acid) films", J. Biomater Science Edn. vol. 9, No. 11, pp. 1187-1205 (1998).

T. Dintelmann et al., "Comparative study of ROS degradation by IPE and RPE cells in vitro", Graefe's Arch Clin. Exp. Opthamology 1999, No. 237, pp 830-839.

C.D. James et al., "Aligned Microcontact Printing of Micrometer-Scale Poly-L-Lysine Structures for Controlled Growth of cultured Neurons on Planar Microelectrode Arrays", IEEE Transaction On Biomedical Engineering, vol. 47, No. 1, Jan. 2000, pp. 17-21.

U. Hartmann et al., "Human and porcine anterior lens capsule as support for growing and grafting retinal pigment epithelium and iris pigment epithelium", Graefe's Arch Clin Exp Ophthalmology (1999), vol. 237, pp. 940-945.

G. Thumann et al., Transplantation of Autologous Iris Pigment Epithelium After Removal of Choroidal Neovascular Membrances, Arch Ophthalomology (Oct. 2000), vol. 118, pp. 1350-1355.

L. Lu et al., "Retinal pigment epithelial cell function on substrates with chemically micopatterned surfaces", Biomaterials (Dec. 1999), vol. 20, No. 23/24, pp. 2351-2361.

A. Lappas et al., "Clinical investigation: Iris pigment epithelial cell translocation in exudative age-related mascular degeneration, A pilot study in patents", Graefe's Archive for clinical Experimental Ophthalmology, Abstract, vol. 238 issue, p. 1 and 2 electronic version, ISSN: 1435-702X, http://link.springer-ny.com/link/service/journals/00417/bibs/0238008/02380631.htm.

Giordano et al., "Retinal pigment epithelium cells cultured on synthetic biodegradable polymers", (Abstract), http://www.ncbi.nlm.nih.gov/entrez/query.fcgi?cmd=Retrieve&db=PubMed&List_uids=897...6.

T. Abe et al., "Auto iris pigment epithelial cell transplantation in patients with age-related macular degeneration: short-term results", (Abstract), http://www.n.../query.fcgi?cmd=Retrieve&dblist=PubMed&List_uids=10896035&dopt=Abstrac.

T. Abe et al., "Functional analysis after auto iris pigment epithelial cell transplantation in patients with age-related macular degeneration", (Abstract), http://www.n.../query.fcgi?cmd=Retrieve&db=PubMed&List_uids=10739164&dopt=Abstrac.

J. Nicolini et al., "The anterior lens capsule used as support material in RPE cell-transplantation", (Abstract), http://www.ncbi.nlm.gov/entrez/query.fcgi?cmd=Retrieve&db=PubMed&List_uids=11C...7.

Sandyk, R. "Paroxysmal Itching in Multiple Sclerosis During Treatment with External Magnetic Fields" (1994) Published in Int. J. Neurosci. 75(1-2): 65-71.

Heuschkel, M.O. et al. Buried Microchannels in Photopolymer for Delivering of Solutions to Neurons in a Network. (1998) Published in Sensors and Actuators B 48: 356-361.

Yeung, C.K. et al. "Modulation of the Growth and Guidance of Rat Brain Stem Neurons Using Patterned Extracelluar Matrix Proteins." (2001) Published in Neuroscience Letters 301: 147-150.

Maher, Michael et al. "The Neurochip: A New Multielectrode Device for Stimulating and Recording from Cultured Neurons" (1999) Published in Journal of Neuroscience Methods 87: 45-56.

Jenkner, Martin et al. "Interfacning a Silicon Chip to Pairs of Smail Neurons Connected by Electrical Synapses" (2001) Published in Biol. Cybern 84: 239-249.

Seneinejad, Samar et al. "Patterned Glass Surface Direct Cell Adhesion and Process Outgrowth of Primary Neurons of the Central Nervous System" (1998) Published in J. Biomed. Mater. Res. 42: 13-19.

Tai, Hsin-Chien et al. "Neurite Outrgrowth and Growth Cone Morphology on Micropatterned Surfaces" (1998) Published in Biotechnol. Prog. 14: 364-370.

Litke, A.M. "The Retinal Readout System: A Status Report" (1999) Nuclear Instruments and Methods in Physics Research A 435: 242-249.

Mayne, A.H. "Biologically Interfaced Porous Silicon Devices" (2000) Published in Phys. Stat. Sol. 182: 505-513.

* cited by examiner

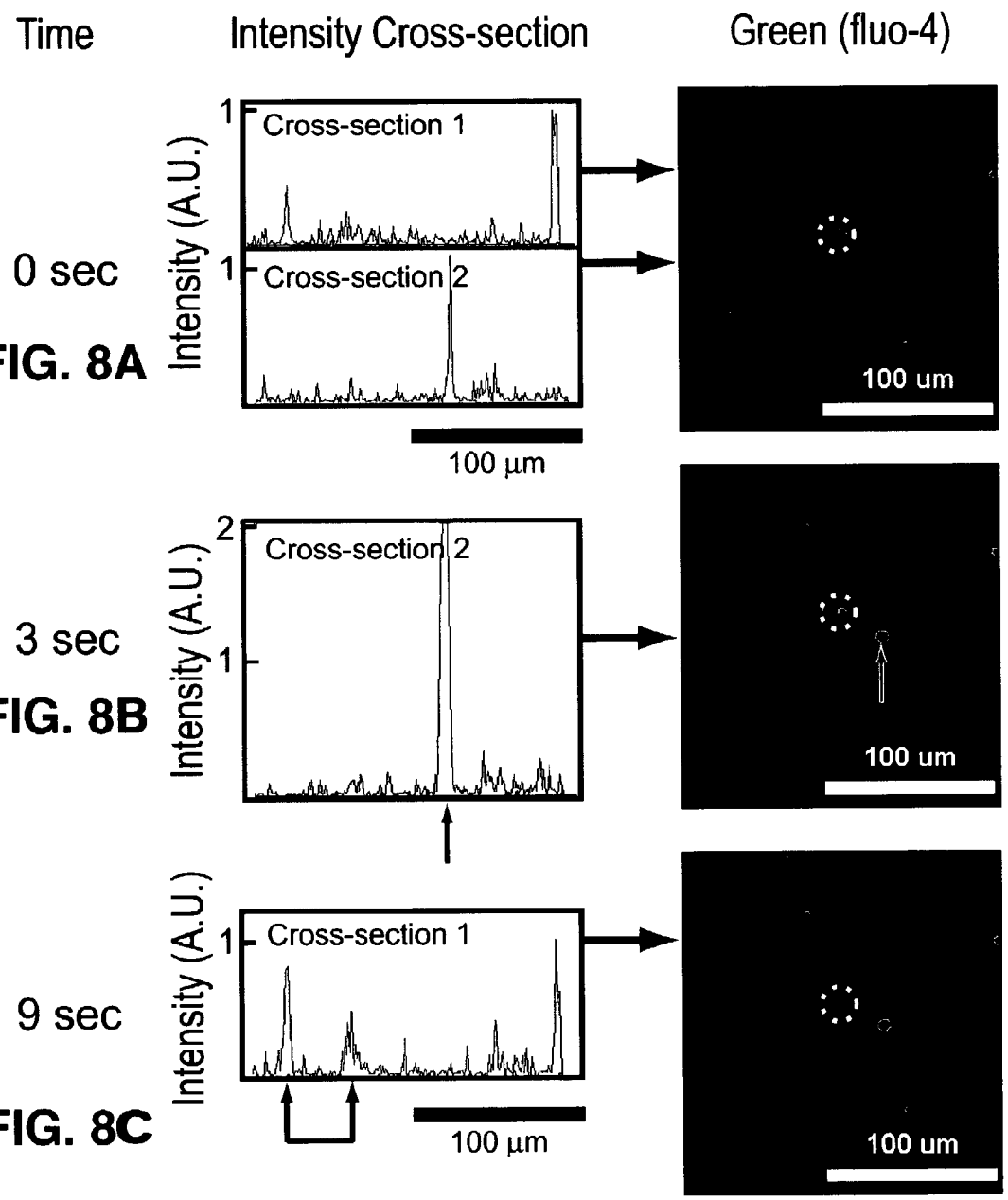

ARTIFICIAL SYNAPSE CHIP INTERFACE FOR ELECTRONIC PROSTHETIC RETINA

CROSS REFERENCE TO RELATED APPLICATION

This application is related to and claims priority under 35 U.S.C. § 119(e) from U.S. Provisional Application Serial No. 60/301,934, entitled "ARTIFICIAL SYNAPSE CHIP INTERFACE FOR ELECTRONIC PROSTHETIC RETINA", by Fishman et al., filed Jun. 29, 2001, which is hereby incorporated by reference in its entirety.

FIELD OF THE INVENTION

The invention pertains to the devices for controlling cell growth and for stimulating cells. In particular, the invention is directed to methods and devices for controlling neuronal growth to provide artificial synapses and neural prostheses.

BACKGROUND OF THE INVENTION

Light entering the eye through the cornea is focussed through the lens (which further focuses the light) onto the retina, a thin layer of cells in the back of the eye. Normal human vision depends upon signals generated by nerve cells in the retina. The visual signals originate with the photoreceptor cells in the retina, which sense and respond to light, generating signals that in turn create and shape nerve signals in retinal ganglion cells. Nerve cells often have extended cellular portions called cell processes, which may be specialized for receiving information and stimulation, or for transmitting information. For example, the specialized elongated processes that conduct nerve impulses are termed axons. The axons of the retinal ganglion cells carry the visual signals from the retina to the brain. In the brain, nerve cell networks process the visual signals further to provide the full visual experience of a normally-sighted person. Disturbances at any step in the process may lead to visual impairment or blindness.

Age-related macular degeneration (AMD) is one of the most common forms of blindness in people over the age of 65. Currently, there is no effective treatment for most patients with AMD, a disease that often results in permanent damage to photoreceptors, but spares most retinal ganglion cells (RGCs). Similarly, other diseases such as retinitis pigmentosa (RP) cause vision impairment and blindness due to loss of photoreceptors.

Inherent to the power of the human visual system is the ability to transduce light by individual photoreceptors, thus making it a high-resolution image capture system. Several groups worldwide have carried out clinical experiments to determine if stimulating retinal cells, the optic nerve bundle, or cells of the visual cortex with microelectrode arrays can generate phosphenes (i.e., sensations of light) in individuals blinded from AMD. The electrical fields produced by the microelectrode arrays stimulate relatively large regions containing numerous neuronal and glial cells. These trials have shown that by stimulating neurons with a microelectrode array, blind individuals can indeed recognize a simple pattern such as a horizontal or vertical line. Although these trials have demonstrated that vision is recoverable in a limited fashion, major challenges remain. Due to the size and difficulties in placement of most available electrodes, imprecise electric field stimulation extending over long distances (several cell-body diameters) is used to depolarize neurons. However, such methods often require excessive stimulation, which may be harmful, leading to inflammation of the stimulated region and even to excessive growth of glial cells, or gliosis. Thus, an unmet major challenge of these approaches is that of constructing a neural interface that stimulates localized retinal regions, individual neurons, and even specialized portions of neurons with specificity.

Neurons may be grown on artificial substrates. However, the synaptic connections of neurons grown on artificial substrates may not be controlled or precisely directed to defined locations, and do not provide for the specific stimulation characteristics found in vivo.

Accordingly, methods and devices are needed that improve the specificity of neural stimulation, and preferably improve the specificity of neural stimulation with low power delivery to avoid gliosis and inflammation.

SUMMARY OF THE INVENTION

The invention combines micropatterned neuronal growth with a microfabricated stimulation interface to form a new neuronal regeneration electrode that serves as an artificial synapse, the device being termed an artificial synapse chip (ASC). A "regeneration electrode" is made by regenerating a nerve fiber into an electrode. The artificial synapse provides a microfabricated aperture (a "nanoaperture") that connects a neuronal cell process (a neurite) to a chemical or electrical means of neuronal excitation. The nanoaperture mimics the length scales of a real synapse and thus emphasizes the localized spatial relationship between the neuron and the stimulation source.

The inventors have recognized that the problem of the development of a neural interface that preserves the high resolution, one-to-one registry with individual neurons and with low power delivery can be broken down into two puts: first, bringing the nerve and the stimulation source together, second, stimulating the nerve cell itself. The ASC combines directed, micropatterned neuronal growth with a neural stimulation source to provide low-power stimulation (nano-stimulation) of at least a part of a desired neuronal cell. Thus, the ASC is not only effective to act as a substrate on which to direct the growth of neurites from nerve cells to a stimulation source, but is effective to serve as a stimulation source as well.

The invention is thus directed to devices and methods for controlling the growth of a cell process, which include a substrate with a surface configured for growing cells and cell processes and a micropattern effective to control the growth of cells and cell processes in a desired direction to a desired location or locations on the surface. A desired location may be a nanoaperture, an electrical contact, or a micropattern feature. The micropattern may include chemo-attractant factors, adhesion molecules, repulsive molecules, surface contours, and/or at least one region enriched in particular atoms. The micropattern may be produced by contacting a substrate surface with a microcontact printing stamp. Devices having a surface with such a micropattern embodying features of the invention may be used to control the growth of cell processes by contacting a cell with the surface, effective to control the growth of a cell process in a desired manner. Contacting a cell with a surface having a micropattern, directing the growth of a cell process to a desired position on the surface, and providing a stimulus from the desired location to a cell process is effective to stimulate at least a portion of the cell.

A device for contacting and stimulating a cell may have a surface configured for contacting at least a portion of a cell, and may have at least one contact in electrical continuity with a circuit. Such a device is effective to stimulate at least a portion of a cell, and is particularly suitable for the stimulation of a neurite. For example, the devices may be used to stimulate a cell or cell process adjacent an electrical contact by way of stimulation of a neurite, stimulation of a cell through a neurite, or stimulation of a cell body.

The invention also provides methods for directing the growth of a cell process to a location adjacent a contact of a circuit. The growth of a cell process may be directed to a location adjacent the contact by contacting a cell capable of growing a cell process with a surface that has a circuit and a micropattern. The micropattern may include factors such as chemo-attractant factors, adhesion molecules, repulsive molecules, surface contours, and/or have at least one region enriched in particular atoms. The micropattern for directing the growth of a cell process may be produced by a method including contacting a surface with a microcontact printing stamp. The growth of a cell process may be directed by delivering a neuromodulatory agent to at least a portion of a cell. Desired locations towards which growth may be directed include a nanoaperture, a contact of an electrical circuit, and a surface feature.

Devices embodying features of the invention may include a surface with a nanoaperture, and a reservoir that may contain neuromodulatory agents, such as neurotransmitters, hormones, ions, messenger molecules, nucleic acids, nucleic acid vectors, drugs, cells, cell fragments, cell organelles, liposomes, or other biologically active materials. The nanoaperture is effective to provide a conduit for the delivery of the neuromodulatory agents from the reservoir to at least a portion of a cell. A device for delivering neuromodulatory agents may have an exterior surface with a micropattern effective to direct the growth of a cell process as described above. Thus, microfabricated artificial synapse chips include microfabricated devices having a nanoaperture, a surface with a micropattern effective to direct the growth of a cell process so as to contact the nanoaperture, and a reservoir which may contain neuromodulatory agents connected to the nanoaperture.

A reservoir may be directly in contact with a nanoaperture, or may be connected to a nanoaperture by a conduit effective to deliver neuromodulatory agents from the reservoir to the nanoaperture. Pumps or other fluid-directing mechanism may be operably connected to a reservoir and/or conduit effective to induce fluid flow which may, for example, be effective to aid the delivery of neuromodulatory agents to the nanoaperture.

Delivery of a neuromodulatory agent may be effective to provide a stimulus to a cell. Embodiments of the invention provide methods for providing a stimulus to a cell process effective to stimulate at least a portion of a cell. In embodiments of the invention, methods of cell stimulation include stimulating a cell process, stimulating a cell through a cell process, and stimulating a cell body.

In other embodiments, the invention provides a regeneration electrode assembly that includes a neurite-directing device and a circuit effective to contact and stimulate at least a portion of a cell. The neurite-directing device may include a device for directing the growth of the cell process, a device for delivering neuromodulatory agents to at least a portion of a cell, or both. The circuit may include a device for contacting and stimulating at least a portion of a cell, or a cell process, or a cell body.

The ability to direct neurite extension to form directed contacts with a circuit is useful in therapies for any disease of neural tissue. Thus, in one aspect of the invention, the devices and methods provide a neural interface that can bypass retinal photoreceptors and connect a digital camera to individual nerve cells in the retina. In this way, cells damaged in AMD and other blinding diseases can be bypassed and visual information sent to the brain. Thus, the artificial synapse chip provides methods for the restoration of visual function in patients suffering from blindness due to age-related macular degeneration (AMD), retinitis pigmentosa, and other photoreceptor blinding diseases. The devices and methods of the invention provide a neural prosthesis suitable for implantation in any location within the nervous system or body of a patient, for the treatment of spinal cord injuries, neuropathies, bladder dysfunction, and other diseases due to neuronal disorders.

Methods of the invention may be used to produce intraocular devices. Devices configured for implantation into an eye embodying features of the invention include a device for contacting and stimulating at least a portion of a cell, and a regeneration electrode assembly configured for implantation into an eye. In embodiments of the invention, devices are configured for implantation into regions of the eye, including the retina, the inner limiting membrane and the subretinal space.

A photosensitive assembly for restoring vision in an eye having decreased photoreceptor function includes a photosensitive device effective to respond to light with photoactivated signals, an artificial synapse chip, a power source effective to power the photosensitive device, and an effective connection between the photosensitive device and the artificial synapse chip. Implantation of a photosensitive assembly provides a method for restoring vision in an eye having decreased photoreceptor function. An eye disorder may be treated by implanting a photosensitive assembly into an eye, directing the growth of retinal neuron cell processes to the photosensitive assembly and stimulating retinal neurons by photoactivated signals derived from the photosensitive assembly.

Devices of the invention, each termed an "artificial synapse chip" (ASC), comprise a high-resolution neural interface to the visual system that incorporates micropatterned neuronal growth to produce an artificial synapse. The nanoapertures of a very small size, guided contacts with desired portions of individual cells, and targeted stimulation of individual cells via these contacts provide a neural interface with high spatial resolution for connecting a circuit to individual neurons. Thus, unlike previous methods for stimulating retinal neurons that offer only poor spatial resolution, the ASC provides the advantages of specificity and control of stimulation at a cellular level to provide novel ways to influence the behavior of a cellular system. In addition, since the source is in direct contact with the neuron, the ASC uses less power for stimulation than prior art field stimulators. The ASC thus provides a new class of regeneration electrodes—one that uses a novel neural interface for stimulation and that uses modern surface science methods for directing neuronal growth so that connection to in vivo neural circuitry in a retina is possible.

BRIEF DESCRIPTION OF THE FIGURES

FIG. 8A illustrates the fluorescence intensity of cells growing on a substrate embodying features of the invention at a time just prior to the flow of a physiological solution containing bradykinin.

FIG. 8B illustrates the fluorescence intensity of cells growing on a substrate embodying features of the invention 3 seconds following the beginning of the flow of a physiological solution containing bradykinin.

FIG. 8C illustrates the fluorescence intensity of cells growing on a substrate embodying features of the invention 9 seconds after the flow of a physiological solution containing bradykinin begins.

DETAILED DESCRIPTION OF THE INVENTION

Figure 1A:
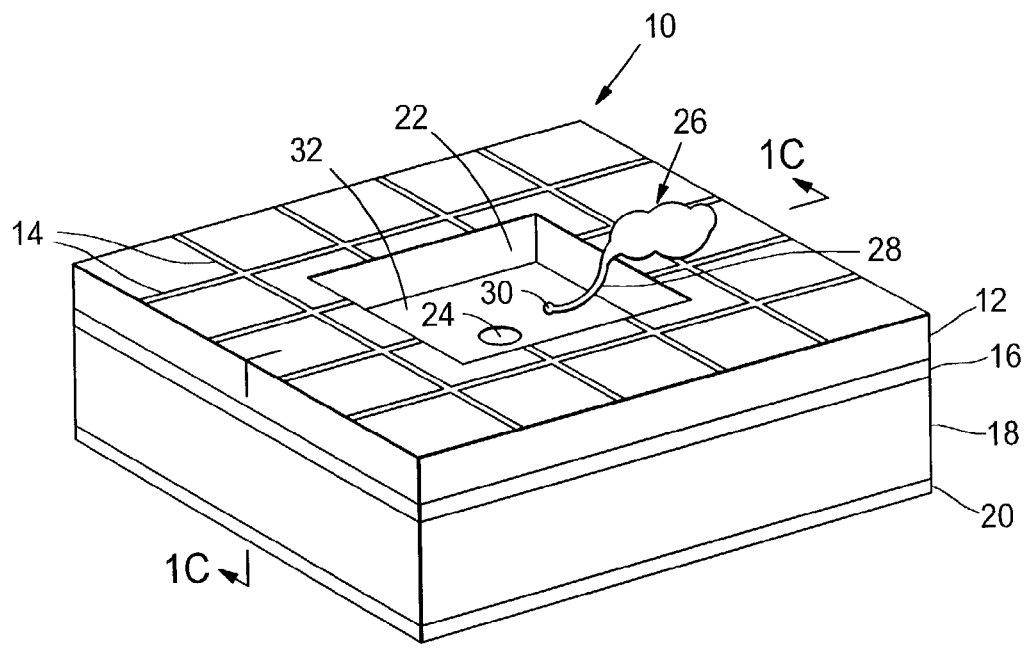
FIG. 1A shows a perspective view of an artificial synapse chip embodying features of the invention.

An artificial synapse chip 10 embodying features of the invention is shown in FIG. 1. FIG. 1A shows a perspective view, and FIG. 1B a plan view of an ASC. The cell-contacting surface of the ASC includes the substrate 12, which may be made with any material or materials compatible with cell attachment and growth. For example, glass, ceramic, silicon, silicon compounds and mixtures, polyimide, polystyrene, polyethylene, polylactide, TEFLON® (Polytetrafluoroethylene—PTFE) or other polymer, are suitable materials. In preferred embodiments, substrate 12 includes polyimide.

A micropattern 14 is provided on substrate 12, effective to direct and guide the growth of cells and cell processes in contact with the substrate 12. The micropattern 14 may be etched into substrate 12, may be deposited onto substrate 12, or may be integral with substrate 12. In preferred embodiments, the micropattern 14 is made by microcontact printing onto the substrate 12. The micropattern 14 may include growth factors, cell adhesion molecules, antibodies specific to cell surface proteins of the neurite or cell body, or other molecules or atoms effective to guide or modulate the growth of a neurite or the attachment of a cell or cell process.

Underlying the substrate 12 is a supporting layer 16. An intermediate layer 18, preferably formed with silicon, is provided adjacent to and below the supporting layer. A base layer 20 is shown lying below the intermediate layer 18, so that intermediate layer 18 is sandwiched between supporting layer 16 and base layer 20. In embodiments of the invention, supporting layer 16 and base layer 20 are formed with silicon nitride.

Silicon and silicon nitride provide stable intermediate and substrate layers, and may be produced and formed with widely available tools and knowledge for fabrication. Techniques for silicon device production are highly reproducible and accurate at the sub-micron level. Additionally, silicon allows for greater control of aperture geometry and location, including the ability to create arrays of apertures.

The devices and methods of the invention may be used to direct the growth of cells and cell processes, and to modulate or stimulate such cells and cell processes. A "cell process" is an elongated portion of a cell extending out from a cell body, or soma, and may be an axon, a dendrite, a neurite, a growth cone, or other elongated growing portion of a cell. A "neurite" is an elongated portion, or process, of a neural cell often forming the leading portion of the neural cell in its growth on a substrate. A "growth cone" is a specialized tip of a neurite that leads the growth or movement of a cell in the direction of the tip. The term "neurite" is used herein to refer inclusively to all neuronal cell processes, including axons, dendrites, and neurites and growth cones together.

Neurites may be extended and retracted from a cell in a variety of directions and at different times. The direction and rate of their growth may be influenced by the substrate, chemical gradients in the environment and along the substrate, electrical fields, hormones, and other physical, chemical and biological influences. As used herein, "growth" of a cell process such as a neurite comprises the elongation and migration are normal actions of these cell processes and may occur spontaneously or may be artificially induced or enhanced. Such growth may be directed by the devices and methods of the invention.

Figure 1B:
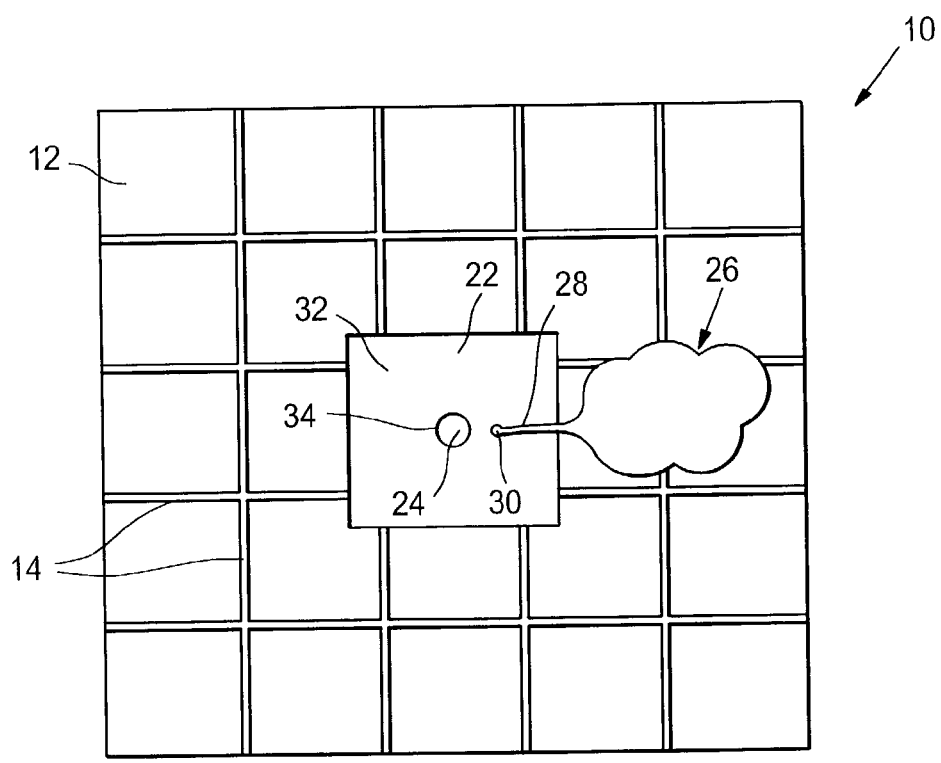
FIG. 1B is a plan view of the artificial synapse chip of FIG. 1A.

Directed growth of a cell process on a device embodying features of the invention is shown in FIG. 1A. A cell 26, with a cell process (neurite 28 with a growth cone 30 at its tip) is shown in contact with substrate 12 and micropattern 14. The path followed by neurite 28 and growth cone 30 on substrate 12 is guided by micropattern 14 so that neurite 28 and growth cone 30 are led to recess 22 and aperture 24. Recess 22 in the substrate 12 leads to an aperture 24 which forms a passage across the supporting layer 16. As shown in FIG. 1B, the floor 32 of recess 22 is formed of supporting layer 16 free of overlying substrate 12. Aperture rim 34, in supporting layer 16 surrounding aperture 24, defines the passageway through supporting layer 16. Although only one cell and only one neurite is shown in FIG. 1A, it will be understood that a plurality of cells, neurites and growth cones may be in contact with substrate 12, recess 22 and aperture 24. A neurite may be directed by the path of micropatterned growth factors to a microfabricated aperture 24, as shown in FIG. 1A.

Figure 1C:
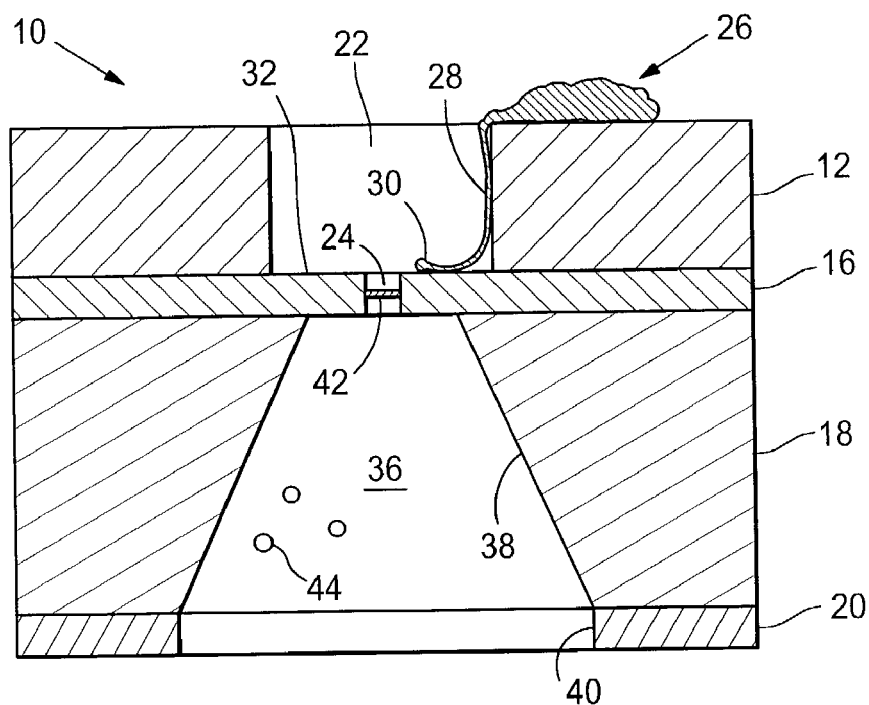
FIG. 1C is a cross-sectional view of the artificial synapse chip of FIG. 1A taken along plane 1C—1C.
Figure 1D:
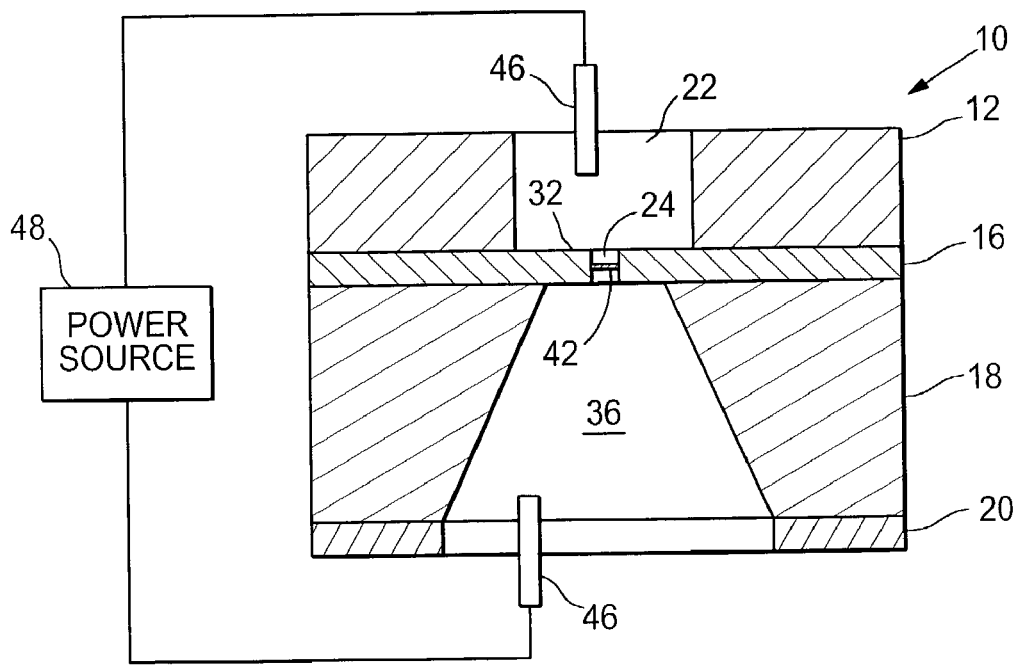
FIG. 1D is a cross-sectional view of an artificial synapse chip as in FIG. 1A taken along plane 1C—1C, illustrating an embodiment of the invention having electrodes.

As shown in FIGS. 1C and 1D, which are cross-sectional views taken along plane 1C—1C of FIG. 1A, aperture 24 opens into reservoir 36 defined by wall 38 of the intermediate layer 18 and wall 40 of the base layer 20. A membrane 42, such as a lipid bilayer membrane, may be formed across aperture 24 to separate reservoir 36 from recess 22.

A membrane 42, in place across aperture 24, may prevent substantially all passage of material between recess 22 and reservoir 36. However, membrane 42 may be a semi-permeable membrane effective to regulate the passage of material through aperture 24 without completely preventing all passage of material. For example, membrane 42 may form a semi-permeable membrane that allows the passage of some atoms, molecules, and ions while restricting the passage of other atoms, molecules and ions. A lipid bilayer membrane has such properties; in particular, a lipid bilayer membrane containing molecules such as ion channels or carriers is able to readily pass specific ions while restricting or substantially preventing the passage of other ions. Lipid bilayer membranes may be formed by Langmuir-Blodgett techniques as is known in the art. See, for example Montal and Mueller, *Proc. Natl. Acad. Sci. USA.* 69:3561–3566 (1972); Montal, *Meth. Enzymol.* 32:545–556 (1974); and Lindstrom et al., *J. Biol. Chem.* 255:8340–8350 (1980).

Recess 22 and reservoir 36 may each contain a solution; the solution in recess 22 may be the same or different from the solution in reservoir 36. The solutions are preferably physiological solutions, such as a saline solution, that is compatible with cell growth and proliferation. Examples of such solutions include phosphate-buffered saline, bicarbonate-buffered saline, HEPES-buffered saline, Dulbecco's Modified Eagle's Medium (DMEM, Sigma Chemical Co., St. Louis Mo., Cat. # D6546), and other solutions known in the art.

The solutions may further contain bioactive agents 44, so that recess 22 and/or reservoir 36 contain bioactive agents. Bioactive agents present within recess 22 and/or reservoir 36 may thus have access to aperture 24 and membrane 42. For example, reservoir 36 may contain hormones, neurotransmitters in liposomes, actual cells, or simply an ionic solution able to be held at an electric potential to stimulate the neuron. Aperture 22 may thus be a stimulation site effective to stimulate a cell by chemical, hormonal, cellular, electronic, or other interactions. In all cases, the stimulation site is very specific to a single cell 26, such as a neuron, and mimics the length scales of chemical synapses or gap junctions in the body.

Bioactive agents 44 may regulate the permeability of the membrane 42, or may be capable of contacting and fusing with membrane 42 effective to deliver agents to the recess 24 from the reservoir 36 or from the recess 24 to the reservoir 36. The bioactive agents are preferably present in reservoir 36 where the bioactive agents 44 are present in only one of recess 24 and reservoir 36. Bioactive agents 44 may include channel forming molecules, such as α-hemolysin, gramicidin, alamethicin, or other channel former; substances such as drugs, neurotransmitters, chemoattractants, hormones, growth factors, adhesion molecules, amino acids, sugars, antibodies, and so forth; dyes; sources of cellular energy; or other compounds. Bioactive agents 44 may be micelles, liposomes, or biological membrane preparations containing ion channels, receptors, or other biologically active molecules that may fuse with and insert molecules into membrane 42. Such bioactive agents may be effective to stimulate cell 26 or to modulate its activity.

An embodiment of the invention having electrodes 46 is shown in FIG. 1D. Electrodes 46 may be made from any of a variety of materials, including silver, silver chloride, chromium, tin, indium, indium tin oxide, zinc oxide, colloidal stamped carbon, platinum, palladium, gold, aluminum, and other elements, oxides and materials known in the art. Electrodes 46 may be used to carry electrical signals from power source 48 to supply current or impose a voltage between electrodes 46 and to stimulate cell 26 or modulate its activity.

Figure 1E:
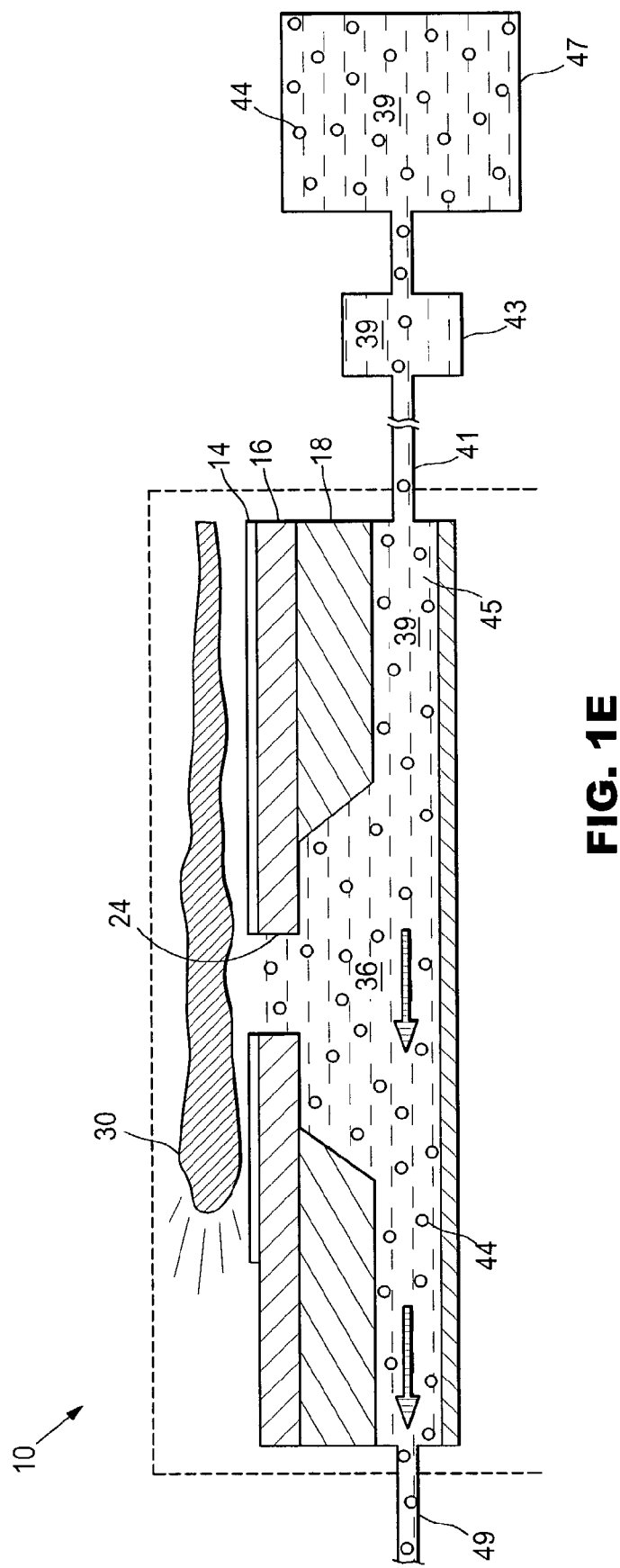
FIG. 1E is a cross-sectional elevation view of a system having a pump and a depot for holding a store of solution and including an artificial synapse chip.

A cell, portion of a cell, or cells growing on an artificial synapse chip having features of the invention may be stimulated by neuromodulators delivered to a reservoir 36 and aperture 24 via a microfluidic delivery system. An artificial synapse chip 10 shown in FIG. 1E is part of a system including a fluid conduit 41 configured to carry a fluid 39 (with fluid flow optionally induced by a pump 43) to a microfluidic channel 45 for delivery to reservoir 36 and aperture 24. A fluid 39 is preferably a biocompatible fluid, such as a saline, preferably including pH buffers to maintain its pH near levels compatible with maintaining cellular health, and may include bioactive agents 44, such as neurotransmitters, neuromodulators, liposomes including neurotransmitters, and other agents that may affect a cell. A supply of fluid 39 may be stored in a depot 47 operably connected to pump 43 and microfluidic channel 45 by fluid conduit 41 or by other means. A fluid 49 may be used to drain or remove excess or waste fluid. A pump effective to cause fluid 39 to flow in a desired direction may be any mechanism suitable for inducing fluid flow. A mechanism for inducing fluid flow may force fluid to flow due to a pressure differential, an osmotic differential, may induce flow by electrical means, including electro-osmotic means, or in other ways.

For example, a pump 43 may include a mechanical pump mechanism, such as a piezoelectric, pneumatic, peristaltic, electrostatic, or electromagnetic pump. Alternatively, or in addition, a pump 43 may include a non-mechanical pump mechanism, in which, for example, fluid force is generated by thermal, chemical (including osmotic), acoustic, magnetic, electric, or electrosomotic, means or mechanisms. Pumps suitable for use with microfabricated devices, particularly electroosmotic pumps, are discussed in Andersson et al., Sensors and Actuators B 72:259–265 (2001); Morf et al., Sensors and Actuators B 72:266–272 (2001); Morf et al., Sensors and Actuators B 72:273–282 (2001); and Zeng et al., Sensors and Actuators B 82:209–212 (2002).

Figure 1F:
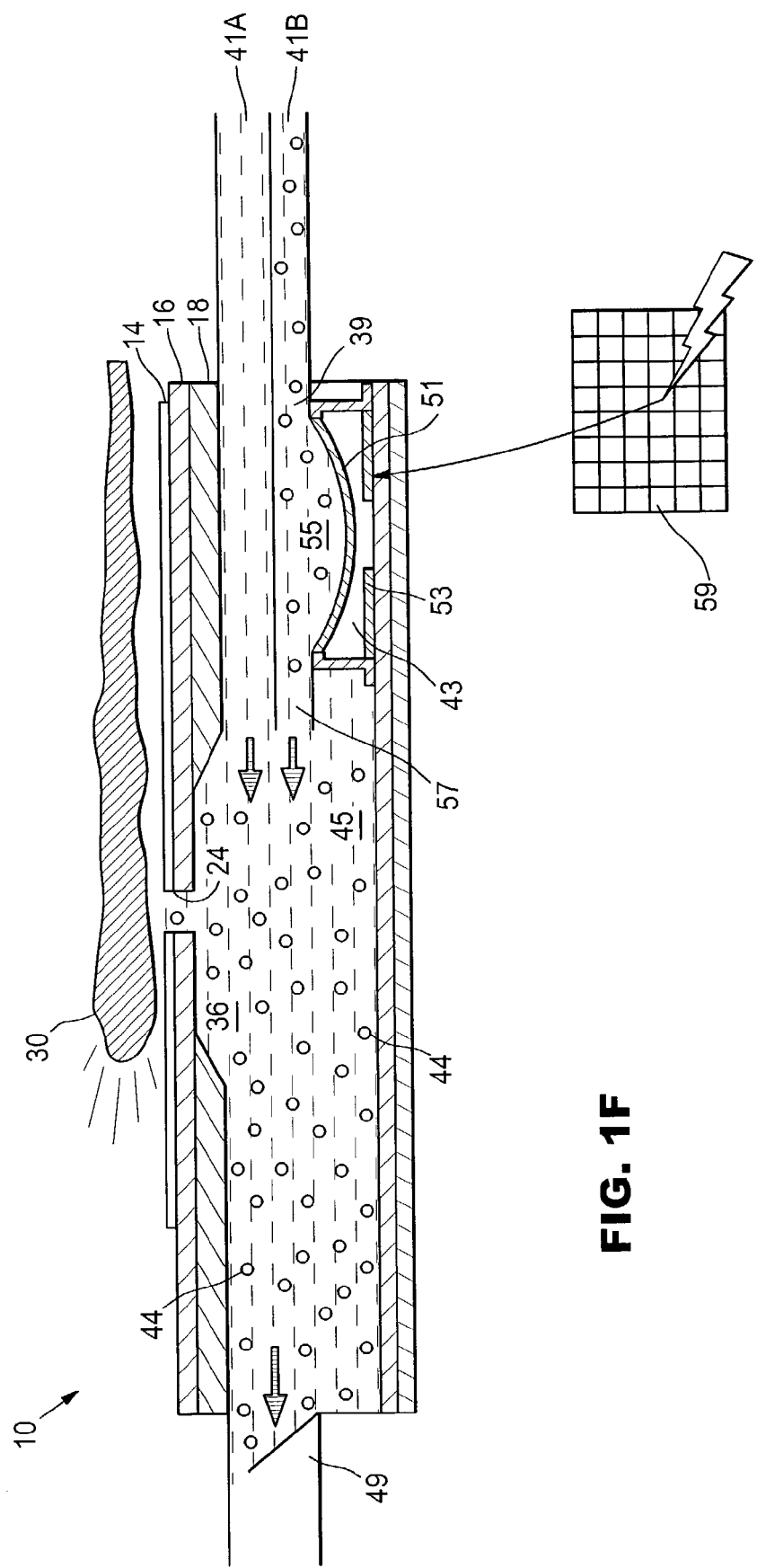
FIG. 1F is a cross-sectional elevation view of a portion of a system having a pump including an artificial synapse chip.

For example, a portion of a system with a pump 43 is illustrated in FIG. 1F. The system includes an artificial synapse chip 10 having a cell with growth cone 30 growing over a pattern 14 on a silicon nitride substrate 16, and a fluid conduit 41 comprised of two-parts, a buffer inlet 41A and a transmitter inlet 41B. Not shown are a depot 47 containing buffer connected to buffer inlet 41A and a depot 47 containing transmitter solution connected to transmitter inlet 41B. The pump 43 illustrated in FIG. 1F is a micro-electro-mechanical (MEM) pump similar to those used in ink-jet printers to eject drops of fluid. Such pumps are described in, for example, U.S. Pat. No. 5,734,395 to Kamisuki et al. A MEM pump as illustrated in FIG. 1F includes of a silicon diaphragm 51, a counter electrode 53, and a microfluidic channel 55 built over the diaphragm structure. The region of the microfluidic channel 55 above the diaphragm 51 is filled with fluid 39 and in fluid continuity with a depot 47 (not shown). The fluid contains bioactive agents 44, which may be, for example, neurotransmitter agents, neuromodulatory agents, synaptosomes, or liposomes containing bioactive agents of any kind. Initially, the diaphragm 51 is in a horizontal (undeflected) configuration. The application of a minute bias voltage between the diaphragm 51 and the counter electrode 53 is effective to deflect the diaphragm 51 downward as shown in FIG. 1F, thereby increasing the volume of the microfluidic channel 55 region above the diaphragm 51 and drawing fluid 39 from the depot 47 along transmitter inlet 41B. Removal of the bias voltage allows the diaphragm 51 to relax back to its initial position, forcing fluid out of microfluidic channel 55 and towards reservoir 36 and aperture 24. Neurotransmitter agents 44 in fluid 39 thus are transported near to reservoir 36, and can diffuse into reservoir 36 and aperture 24 to contact growth cone 30 and affect the cell. In this way, for example, a brief pulse of neurotransmitter agent may be delivered to a cell having a portion growing across an aperture 24. In embodiments of artificial synapse chips, conduit 41 would include simply transmitter inlet 41B; in other embodiments, such as the one illustrated in FIG. 1F, conduit 41 also includes a buffer inlet 41A. Flow of buffer solution through buffer inlet serves to flush out the microfluidic conduit 45 with buffer, carrying away neurotransmitter agents 44, reducing or ending the effect of these agents. Such flushing prepares the system for a subsequent pulse of neurotransmitter agents 44 as well as acting to end the effects of a prior pulse.

Diffusion of neurotransmitter agents 44 through aperture 24 can be very rapid due to the thinness of the aperture, which may be, for example, only about 500 nm thick. The diaphragm 51 of a MEM pump 43 may flex at high frequency so as to eject fluid 39 at high frequency. Pulses of bioactive agents 44 (e.g., neuromodulatory or neurotransmitter agents 44) may be delivered at high frequency, including frequencies ranging from between only a few cycles per second, or Herz (Hz) to about hundreds of kHz. Such rapid signaling matches the rapid signaling rates found in vivo in the brain and retina.

The concentration of bioactive agents 44 is determined by several factors, including the MEM ejector pulsing frequency, the flow rate of fluid through the microfluidic conduit 45, and, where electro-osmotic flow may also be induced, the voltage on the optional buffer chamber electrodes. The concentration of bioactive agents 44 at the aperture 24 is determined in part by the diffusion rate, which is affected by the concentration. The size of a pump 43, such as the ejector diameter determined by the diameter of the outlet 57 of transmitter inlet 41 B, can range from between a few microns ($\mu$m) to hundreds of $\mu$m. The size may depend on the required capacity of a microfluidic channel.

The performance of a pump 43 and a system as illustrated in FIG. 1F depends on the design and materials used, and on the fluids employed during its use. For example, the damping experienced by the system is related to several factors, including fluid viscosity and the geometry of the microfluidic conduit 45, the geometry of the microfluidic channel 55, and the geometry of other components. In order to obtain the desired performance, preferred systems are configured with a diaphragm 51 comprised of polysilicon, a narrow microfluidic channel 55 and a small initial separation between the diaphragm 51 and the counter electrode 53. Since there is no threshold voltage for activating the motion of a polysilicon diaphragm, a MEM ejector pump can deliver small volumes as small as attoliter to zeptoliter volumes. The power required to charge a capacitor of the size of a diaphragm 51 to a fraction of a volt is about a picowatt. A single photodiode, such as an avalanche photodiode capable of generating nanoWatts of power, is thus able to charge hundreds or even thousands of such MEM pumps to deliver bioactive agents to cells.

The power to actuate a pump 43 may thus come from a photodiode in a photodiode array 59 as illustrated in FIG. 1F. Light contacting such an array 59 is thus effective to actuate a pump 43 configured to pump a fluid 39 containing bioactive agents 44 into a microfluidic conduit 45 where the bioactive agents 44 may flow and diffuse through an aperture 24 and into contact with, for example, a growth cone 30 growing across an aperture 24. In this way, for example, an artificial synapse chip 10 may be used to transduce a light signal into a biological signal. An array of artificial synapse chips 10, or an array of systems including such chips, or an artificial synapse chip or chips having an array of apertures, may also be used in similar ways to transduce light signals into biological signals. Alternatively, or in addition, electrical signals may be used to stimulate a cell or cells grown on an artificial synapse chip configured to direct the growth of cells, such as to direct cell growth towards electrodes.

The components and features necessary to construct devices such as an artificial synapse chip 10 may be made using methods commonly termed "microfabrication" or "nanofabrication" techniques. Methods for microfabrication useful for practice of the invention may be found in, e.g., U.S. Pat. No. 5,776,748 to Singhvi et al.; U.S. Pat. No. 5,900,160 to Whitesides et al.; U.S. Pat. No. 6,060,121 to Hidber et al.; U.S. Pat. No. 6,180,239 to Whitesides et al.; "Patterning of a Polysiloxane Precursor to Silicate Glasses by Microcontact Printing", Marzolin, et al., Thin Solid Films 1998,315, 9–12; "Microfabrication, Microstructures and Microsystems", Qin, et al.; In Microsystem Technology in Chemistry and Life Sciences, vol.194, Manz, A. and Becker, H., Eds.; Springer-Verlag, Berlin, 1998, 1–20; "Unconventional Methods for Fabricating and Patterning Nanostructures," Xia et al., Chem. Rev. 99:1823–1848 (1999). All patents and publications, both supra and infra, are hereby incorporated by reference in their entirety. The sophisticated microstructures that may be constructed using such microfabrication methods may be used to make devices such as artificial synapse chips 10 and to modify substrates. The structures shown in the following Figures were made using the Stanford Nanofabrication facility (Leland Stanford Junior University, Stanford, Calif. 94305).

Figure 2A:
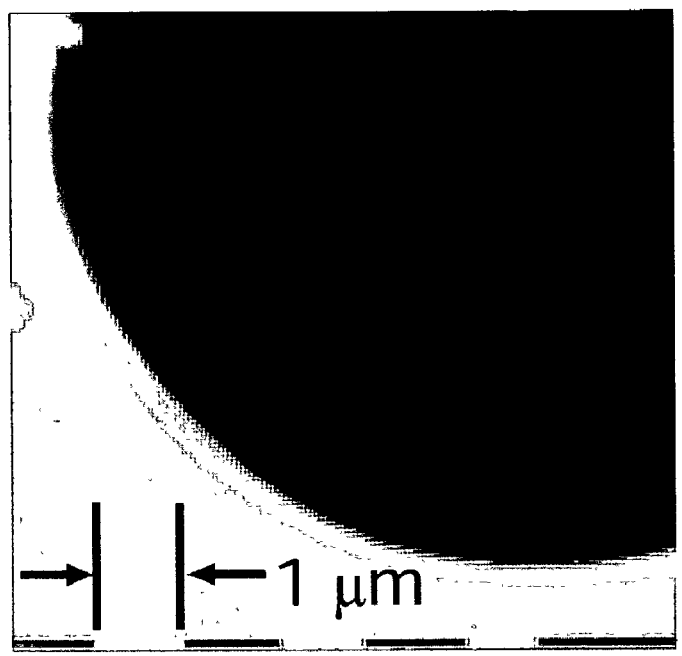
FIG. 2A is a plan view scanning electron micrograph (SEM) of a nanoaperture of an artificial synapse chip embodying features of the invention.

An aperture 24 formed in a silicon nitride supporting layer 16 of an ASC embodying features of the invention is shown in FIG. 2A. The view in FIG. 2A is in the same orientation as the view shown in FIG. 1B, showing the aperture 24 facing the cell-contacting surface of the ASC. The aperture is approximately 10 $\mu$m in diameter (scale bar represents 1 $\mu$m). Aperture 24 is bounded by rim 34 in exposed floor 32 of recess 22. At the small scale shown in FIG. 2A, the aperture 24 is quite smooth, both in terms of shape and surface. To improve resolution, the device was first coated in gold. Note that the plasma etching used for this processing does not create vertical sidewalls in the aperture. The aspect ratio of the sidewalls is roughly 2.5:1. Although the example of the aperture 24 shown in FIG. 2A forms a passageway through a supporting layer 16 made from silicon nitride, other materials may also be used, such as polymers and glass.

A microfluidic reservoir 36 may be connected to the other side of recess 22. A reservoir 36 may be configured to be of a size able to contain neuromodulatory agents in aqueous solution or aqueous suspension. Aperture 24 provides a conduit for the delivery of the neuromodulatory agents from the reservoir 36 to at least a portion of a cell 26. In addition, other conduits and fluidic delivery systems may be used to transport fluid and neuromodulatory agents to desired locations at or adjacent the aperture 24, reservoir 36, or other location. For example, where a depot containing a reserve of fluid and/or neuromodulatory agents is located at a position away from an aperture, a conduit may operably connect the depot with a reservoir 36 and with an aperture 24.

Figure 2B:
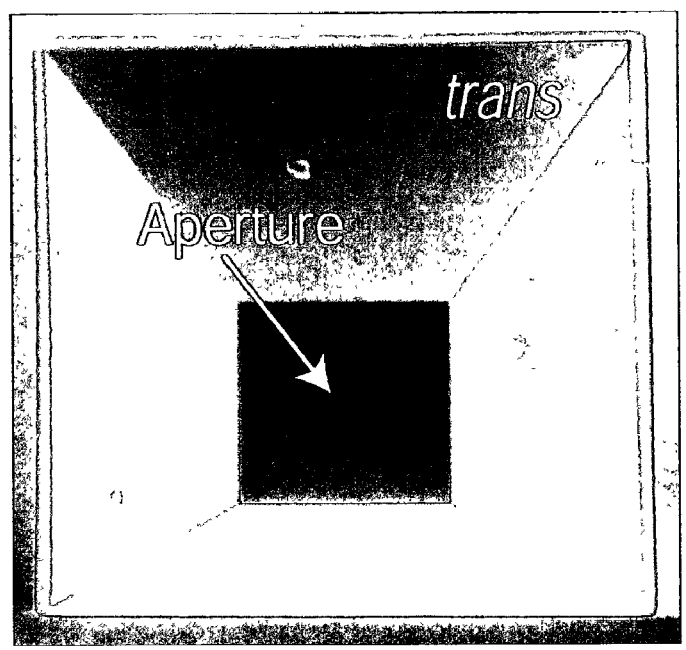
FIG. 2B is a plan view SEM of a reservoir of an artificial synapse chip embodying features of the invention.

FIG. 2B is a scanning electron micrograph (SEM) of a microfabricated well that has a microaperture in the bottom, showing reservoir 36 of an artificial synapse chip embodying features of the invention, viewed from the face opposite to the cell-contacting substrate surface 12 of the ASC. Shown at a larger scale than FIG. 2A, this micrograph of the reservoir 36 viewed from the trans side of the artificial synapse chip 10 shows the smooth silicon nitride surface surrounding the aperture 24. Wall 38 of the intermediate layer 18 and wall 40 of the base layer 20 are shown, with a small amount of base layer 20 shown framing the walls 38 and 40. The black spot indicates the aperture 24 configured for cell attachment and stimulation (not clearly visible at this magnification). The reservoir 36 is designed for holding the culture solution for the cells. The size of the bottom of the well is 1 mm across.

Figure 2C:
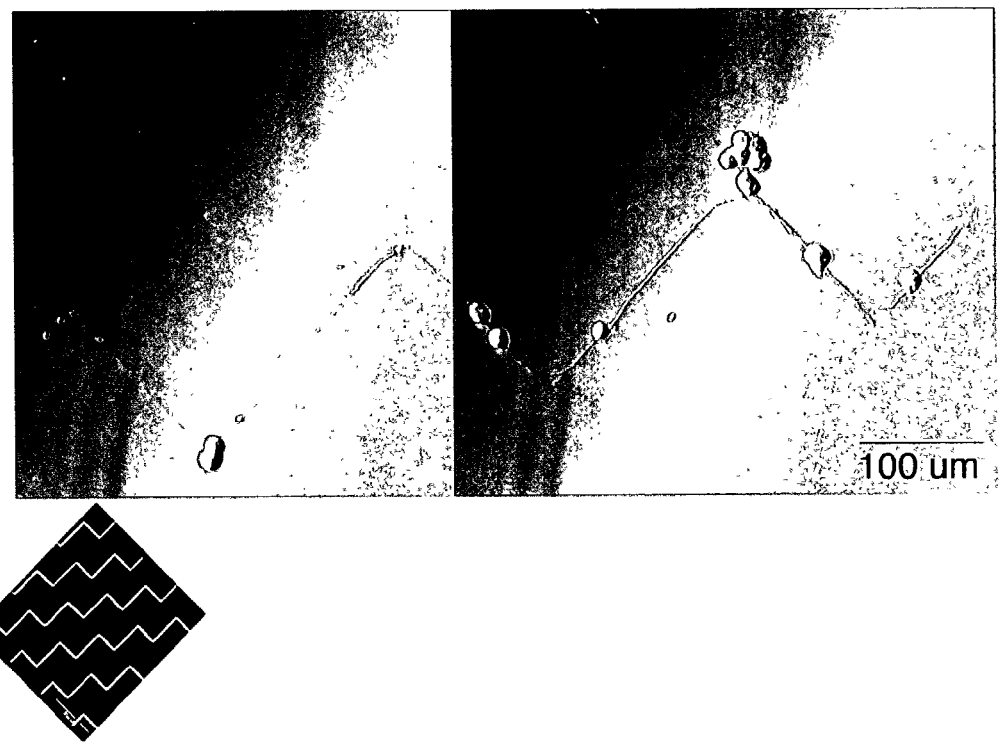
FIG. 2C illustrates patterned growth of retinal ganglion cells on a patterned substrate.

As shown in FIGS. 1A and 1B, a substrate 12 of ASC 10 may have a micropattern 14 effective to guide and direct the growth of a cell process, such as neurite 28 with growth cone 30. Such directed cell growth is shown in FIG. 2C, which is a scanning electron micrograph showing rat P7 retinal ganglion cells (RGCs) grown on a plastic substrate that was patterned with a laminin pattern. The insert at the bottom left of FIG. 2C illustrates the sawtooth pattern microfabricated onto the substrate before addition of the RGCs. As shown in the electron micrograph, both the cell bodies and the cellular processes follow the pattern quite closely. The scale bar represents a length of 100 $\mu$m.

Figure 2D:
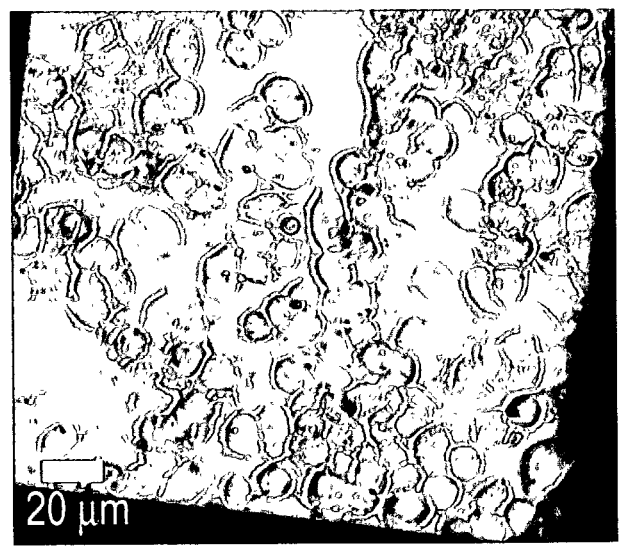
FIG. 2D illustrates growth of PC12 cells around and over a 5 $\mu$m-diameter aperture in a silicon nitride substrate.

Cells are also able to grow over a microfabricated aperture 24 through a supporting layer 16 of an ASC 10. FIG. 2D shows PC12 cells growing around and over a 5 $\mu$m-diameter aperture in a silicon nitride surface. The boundary of a reservoir 36 under the aperture 24 may be seen at the margins of FIG. 2D.

Figure 3:
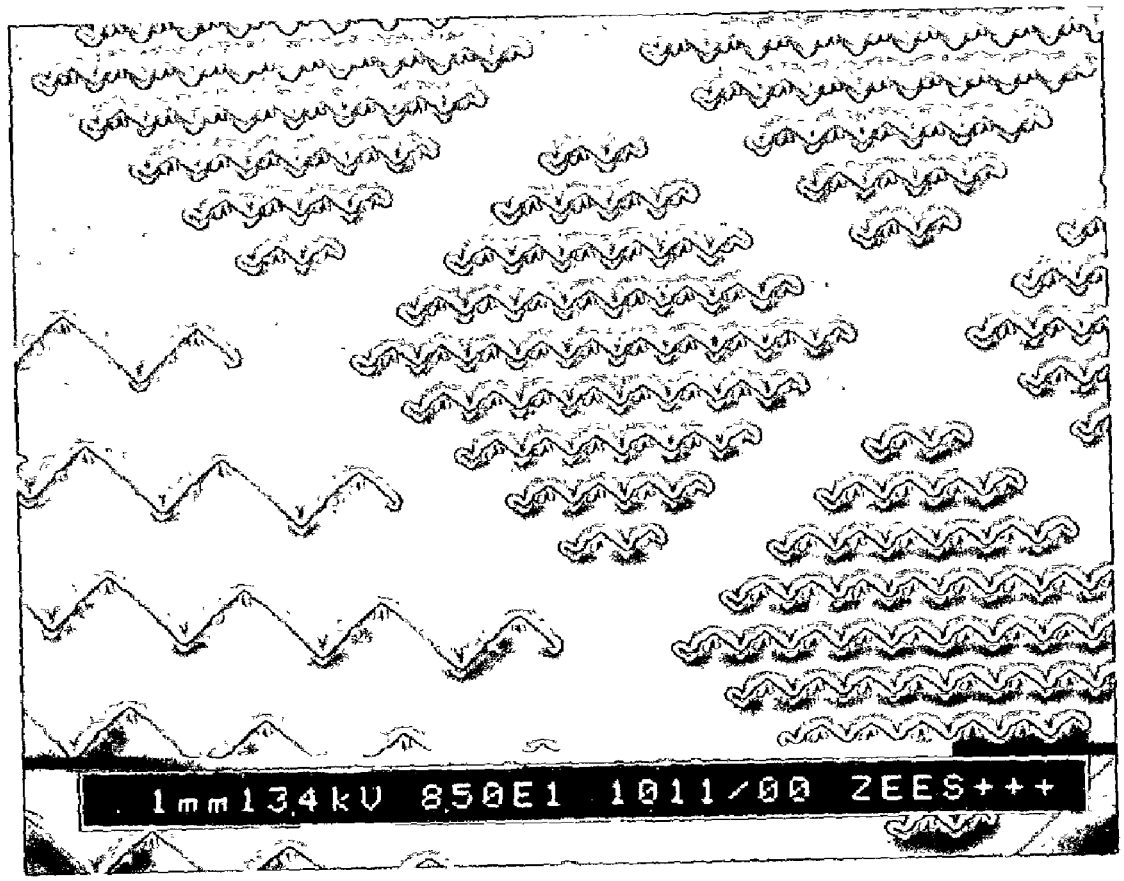
FIG. 3 is a plan view SEM of a stamp embodying features of the invention for making a micropattern on a surface.

A preferred method of producing a micropattern 14 is to contact substrate 12 with a microcontact printing stamp having an ordered assemblage of molecules, which may be a discontinuous assemblage, for deposition on to substrate 12. Microfabrication methods are suitable for making microcontact stamps. FIG. 3 is a plan view SEM of a stamp embodying features of the invention for making a micropattern 14 on a surface. The surface topology is given by the array of squares. Deposition of material onto the surface of a stamp, and contacting a substrate 12 of a device, such as an artificial synapse chip 10 shown in FIG. 1, with the stamp is effective to form a micropattern on a substrate 12. The formation of a micropattern in this way is one method of microcontact printing. Micropatterns formed by such microcontact printing methods are effective to align the position and growth of cells on a substrate. Shown in FIG. 3 is a scanning electron micrograph (SEM) picture of a poly (dimethylsiloxane) (PDMS) stamp that was made from a master that was micromachined from a silicon wafer. The microcontact stamp shown in FIG. 3 has a surface topology given by an array of squares. Other patterns, including circles, ovals, stripes, and other shapes, may be made on the surface of a microcontact stamp.

Microstamps such as the one shown in FIG. 3 may be fabricated using photolithography techniques. For example, the stamp shown in FIG. 3 was formed from a thin (1–7 $\mu$m) photoresist layer on a silicon wafer that was patterned to create a master for the microcontact printing. The mask and stamp master was fabricated at the Stanford Nanofabrication Facility. The master pattern consists of arrays of lines configured for cell attachment and neuron growth. The master was prepared by ultra-violet (UV) etching of a mask on positive photoresist on silicon, and PDMS stamps were generated in situ on the master using Sylgard 184 silicone elastomer followed by thermal curing. Stamps were also prepared by pouring an elastomer and curing agent together to form PDMS on a silicon master, degassed and allowed to set at room temperature. Stamps were then made by cutting a portion of the PDMS followed by plasma treatment to increase hydrophobicity for enhanced protein adsorption and imaged using SEM.

A variety of different stamp patterns may be produced by the methods, and adapted to the optimal line width or thickness, length and spacing for neurite growth. For example, line widths ranging from a few nanometers (nm) wide to several hundreds of micrometers ($\mu$m) wide may be used; preferably, line widths range from about 10 nm to about 20 $\mu$m. Lines may be as short as a few nm and may be as long as several millimeters; preferably line length is within the range of about 10 nm to about 100 $\mu$m long. The spacing between lines in a pattern may range from about 1 $\mu$m to several hundreds of $\mu$m; preferably line spacing is between about 2 $\mu$m to about 100 $\mu$m.

Following microfabrication of the stamps, the stamps were coated with molecules desired to be deposited onto a substrate 12 to provide a micropattern 14. Micropatterns may include biologically active molecules and agents such as neurotransmitters, hormones, growth factors such as nerve growth factors, epidermal growth factor, and insulin-like growth factor, co-stimulatory molecules, antibodies, and other biomolecules known in the art. For example, stamps may be coated with adhesion agents that promote call adhesion. Adhesion agents include poly-L-lysine, CELL TAK™ (Cell and tissue adhesive: Becton Dickinson, Franklin Lakes, N.J.), cell adhesion molecules such as neural cell adhesion molecule (NCAM), lectins, and other adhesion agents known in the art. The adhesion agents may also be labeled with fluorescein for visualization. The pattern may be stamped on glass, silicon, silicon nitride, polyimide, polystyrene, polyethylene, polylactide, TEFLON® (Polytetrafluoroethylene—PTFE), other polymer, or any substrate suitable for use as a substrate for cell growth. For example, a coated stamp may be contacted with a polyimide substrate on a silicon nitride supporting layer to provide a substrate to facilitate cell adhesion and growth. Cell adhesion and growth may be monitored with a fluorescence microscope. A mercury arc lamp may be used to excite the fluorescent dye conjugated to the poly-L-lysine or other micropattern molecule to provide fluorescence signal for visualization of adhesion agents.

Figure 4:
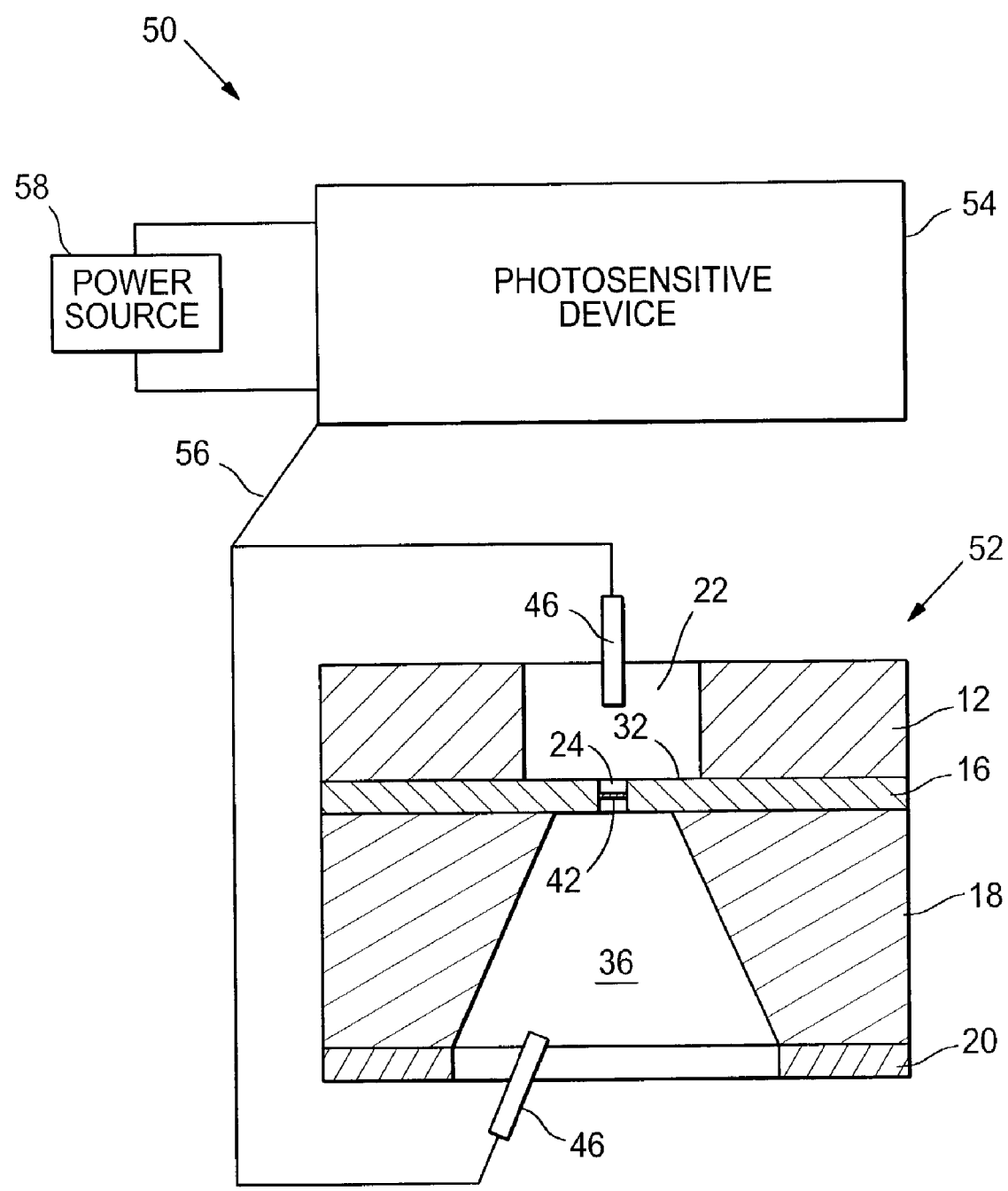
FIG. 4 is a system for implantation of an artificial synapse chip into an animal comprising artificial synapse chip (ASC), a photosensitive device, a means of communication between the ASC and the photosensitive device, and a power source.

A system 50 for implantation into an animal is shown in FIG. 4. In embodiments, the system is implanted into the retina of an animal. The system 50 includes an ASC 52, a photosensitive device 54, a communication link 56 between the ASC and the photosensitive device, and a power source 58. The photosensitive device 54 may be separate from the ASC 52, or may be in contact with the ASC 52, or may comprise part of the ASC 52. The photosensitive device 54 may be a photomultiplier, a semiconductor photosensor, a chemical photosensor, a metallic photosensor such as a selenium or other photocell, or other photosensor known in the art. The communications link 56 may be any electrical conductor, such as a wire, tracing, or other electrical link. In embodiments, the communications link 56 is a chemical communications link, whereby a photosensor alters the chemical environment so that a chemical signal is delivered to at least a portion of the ASC 52. The power source 58 may be any power source, such as a battery, a thermal power source capable of producing power by a temperature gradient, or a photocell capable of producing energy from light.

Figure 5A:
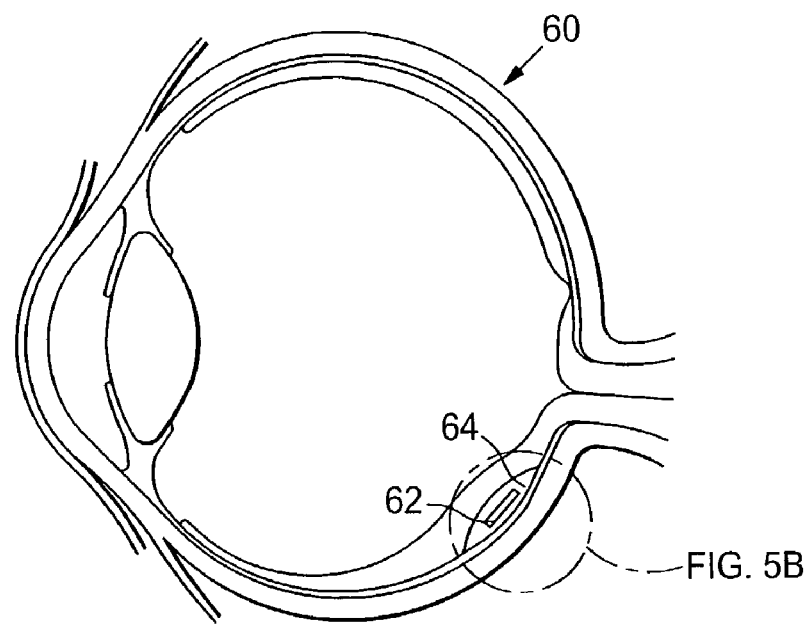
FIG. 5A illustrates a cross-section of an eye of animal with an implanted ASC.
Figure 5B:
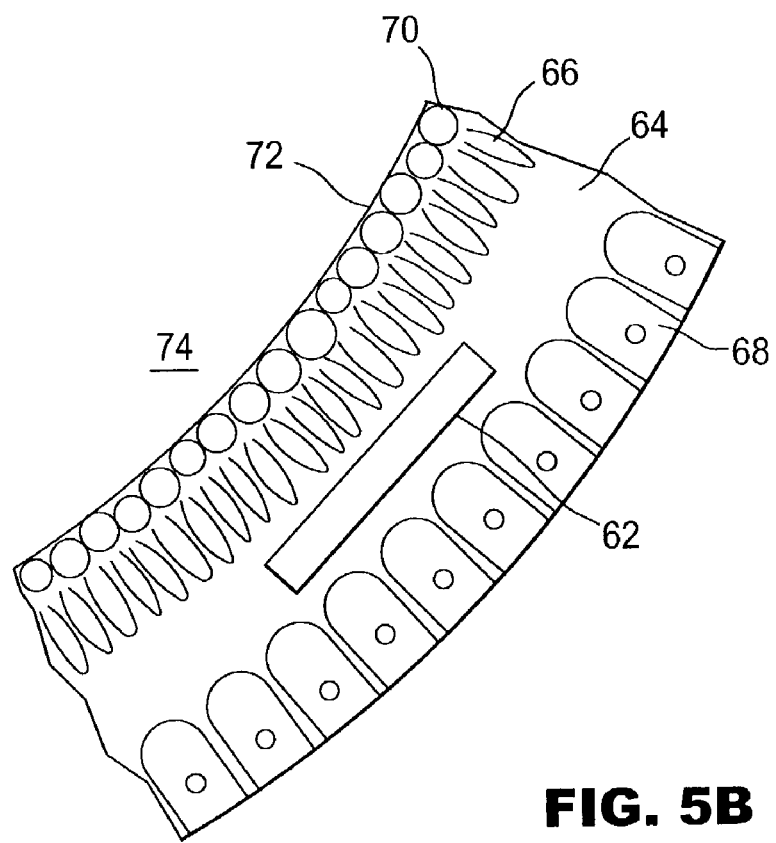
FIG. 5B is a detailed cross-sectional view showing the eye of FIG. 5A and the ASC in place in the subretinal space of the eye.

FIG. 5A illustrates an eye 60 of animal into which an ASC 62 has been implanted. The ASC 62 is shown implanted in the subretinal space 64 of the animal, so that it occupies a position between the retinal photoreceptors 66 and the retinal pigment epithelium 68. In embodiments of the invention, the ASC 62 may be implanted near the ganglion cell layer 70 on the inner limiting membrane 72 near the boundary of the vitreous humor 74. A detailed view of the subretinal space 64 and implanted ASC is shown in FIG. 5B.

ASCs may be used for implantation into the nervous system of an animal. For example, ASCs embodying features of the invention may be implanted into a retina of an animal to provide a neural prostheses where the retina suffers from traumatic injury, disease or degeneration. Patterns may include one or a combination of molecules such as neurotrophins and growth factors including nerve growth factor, brain-derived growth factor (BDGF), epidermal growth factor (EGF), ciliary neurotrophic factor (CNTF), glial-derived neurotrophic factor (GDNF), NT-3, fibroblast growth factors (FGF), insulin-like growth factor (IGF), platelet-derived growth factor (PDGF), vascular endothelial growth factors (VEGF) and others; cyclic nucleotides such as cyclic adenosine monophosphate, cyclic guanosine monophosphate and others; extracellular matrix molecules such as laminin, tenascin, collagen, fibronectin, integrins, immunoglobins (including molecules such cell adhesion molecules N-CAM and L-CAM, axonin, cadherins, and so forth), proteglycans, anosmin-1, thrombospondin and others; myelin and myelin associated inhibitors such as myelin-associated glycoprotein and nogo; tyrosine kinase receptors such as ephrins; netrins; inflammatory cytokines such as transforming growth factor δ, leukemia inhibitory factor (LIF), tumor necrosis factors (TNF), interleukins, and others; neurotransmitter such as acetylcholine and others; stimulatory molecules such as potassium chloride, insulin, and others; co-stimulatory molecules, antibodies, and other growth and modulatory factors known in the art.

It is critical to optimize the retention of the pattern for transfer from the stamp to the cellular system for use of the substrate in implantation, such as retinal implantation. The line width and concentration of biomolecules may be used to control the number of neurites per microprinted line. The degree of pattern transfer may be determined using microscopy.

As shown in FIG. 1, the recesses 22 and reservoirs 36 of the devices of the present invention are suitable for the storage of neuromodulatory agents, and for the delivery of neuromodulatory agents to at least a portion of a cell. The present invention provides the ability to direct the delivery of neuromodulatory agents to single cells, in particular to localized portions of such cells, by directing the growth of cell processes to nanoapertures, and delivering neuromodulatory agents to the cell processes via the nanoapertures. Suitable neuromodulatory agents include any agent effective to stimulate a cell, or to modulate the effects of other agents effective to stimulate a cell. For example, the neuromodulatory agents may be neurotransmitters, hormones, ions, messenger molecules, nucleic acids, nucleic acid vectors, drugs, cells, cell fragments, cell organelles, liposomes, or other biologically active materials. Neuromodulatory agents such as neurotransmitters include amino acids such as glutamate, aspartate, and glycine, and related neurotransmitters and stimulatory agents such as N-methyl-D-aspartate (NMDA), alpha-amino-3-hydroxy-5-methyl-4-isoxalone propionic acid (AMPA), quisqualate, and kainate, and analogs thereof, and other glutaminergic and glycinergic agents known in the art; cholinergic agents such as acetylcholine, suberyldicholine, analogs thereof and other cholinergic agents known in the art; adrenergic agents such as dopamine, epinephrine, norepinephrine, analogs thereof, and other adrenergic agents known in the art; serotinin, and serotonergic agents known in the art; gamma-amino butryic acid (GABA) and other GABA-ergic agents known in the art; taurine, octopamine, nucleotide phosphates such as adenosine triphosphate (ATP), adenosine diphosphate (ADP) and guanosine diphosphate (GDP) and triphosphate (GTP), cyclic nucleotides such as cyclic adenosine monoposphate (cAMP) and cyclic guanosine monophosphate (cGMP), and other neurotransmitter and neuromodulator molecules known in the art. In addition, neurotransmitters include all agents active at neurotransmitter receptors, such as glutamate receptors, NMDA-receptors, AMPA-receptors, glycine receptors, dopamine receptors, acetylcholine receptors, and others known in the art. Neuromodulatory agents also include messenger agents including peptide hormones and neuromodulators such as enkephalins, endorphins, adrenocorticotrophin hormone (ACTH), vasoactive intestinal peptide (VIP), and other peptides known in the art, steroid hormones, second messengers such as inositol phosphates, and ions such as calcium, potassium, zinc and salts thereof. These agents may be free in aqueous solution or aqueous suspension, may be present in micelles, or may be carried by liposomes.

Liposomes, as is known in the art, are small membranous vesicles suitable for delivery of both hydrophilic and hydrophobic compounds. Pharmaceutical administration systems based on liposomes are described in, e.g., Gregoriadis, G. (editor) Liposome Technology, Vol. II, Incorporation of Drugs, Proteins and Genetic Material, CRC Press 1984, and in Knight, C. G. (editor), Liposomes: From Physical Structure to Therapeutic Applications, Elsevier 1981. Neuromodulatory agents suitable for the practice of the invention further include biological membrane preparations containing ion channels, receptors, or other biologically active molecules, as described in, e.g., Coronado et al. J. Gen. Phys. 76:424–446 (1980). Such biological membrane preparations may fuse with and insert molecules into a membrane 42 across an aperture 24, or into the membrane of a cell 26, neurite 28 or growth cone 30. For example, gramicidin, alamethicin, and other molecules known in the art are suitable pore-forming molecules for the practice of this embodiment of the invention. Ion channel molecules suitable for the practice of the invention include multi-subunit macromolecule assemblies such as ligand-gated ion channels including cyclic nucleotide-gated channels, calcium-activated channels, ACHR ion channels, glutamate receptor ion channels, including all NMDA, AMPA, quisqualate, kainate subtypes, glycine receptor ion channels, and voltage-gated ion channel molecules and multi-subunit macromolecular assemblies such as sodium channels, potassium channels, calcium channels, chloride channels, and other channels, including gap junction channels, mechanosensitive channels, non-gated, and non-selective channels. Carrier molecules such as amphotericin are also suitable. Alternatively, membranes may be formed with proteins, such as pore-formers and carriers, already incorporated as part of the membrane-forming material. See, e.g., Schindler, Methods Enzymol. 1989:171:225–253.

EXAMPLE 1

Microfabrication of Apertures

Microfabricated apertures on a silicon chip surfaces have been made using the Stanford Nanofabrication Facility. Microfabricated wells with microfabricated apertures are shown in FIG. 2. Standard silicon processing techniques were adapted for producing micrometer and nanometer-sized apertures in a silicon nitride membrane. Using low-pressure chemical vapor deposition (LPCVD), silicon nitride was grown on the surface of <100> orientation silicon wafers. A combination of lithography to define the structures in a photosensitive polymer was followed by plasma etching to pattern the structures in the silicon nitride creates apertures on one side of the wafer and an etchant masking layer on the other side. An anisotropic etchant, such as tetramethylammonium hydroxide (TMAH), was used to remove the silicon along the {111} crystal plane, but leave the silicon nitride unaffected. This produced a via hole (a connecting passageway) beneath the aperture, exposing the silicon nitride membrane and completing the processing.

Shown in FIG. 2A is a SEM of the microfabricated container. Note the black spot indicated by the arrow is the microetched aperture adapted for cell attachment and stimulation. The well was designed for holding the culture solution for the cells. The size of the bottom of the well is 1 mm across. FIG. 2B shows the microaperture in the bottom of the container shown in FIG. 2A. The microaperture is approximately 10 $\mu$m in diameter. Although not shown, the other side of the aperture is connected to a microchannel reservoir that is made by sealing a PDMS stamp with microchannels to the underside of this substrate.

The conduit, or via, opens into a microfluidic channel that serves as a reservoir for neuromodulatory agents that may be applied to cells adherent to the substrate. The microfluidic channel was made from a standard PDMS stamp as described above and sealed to the wafer. Such a microfluidic channel can be readily sealed to the wafer with excellent sealant properties. For example, a PDMS stamp having a channel may be bonded to a silicon nitride surface after acid cleaning (e.g., HCl) and plasma treating, forming an irreversible bond. The microfluidic channel described has wide ranging ramifications for use including (1) acting as general purpose buffer reservoir for constant replenishing/exchanging waste products from the other side of the cell (2) delivery of transmitters, liposomes, voltage/current clamping of the cell, or (3) for sampling released products from the cell.

Apertures may be formed in sizes ranging from a few nm to a few tens of $\mu$m over which cells may be grown. For example, cells may be grown directly over 50 nm apertures. Use of an aperture smaller than the length scale of the neuron is effective to insure that only a single cell is stimulated.

EXAMPLE 2

Device Fabrication and Optimization

This Example describes the manufacture and optimization of devices embodying features of the invention for use in forming bilayer membranes across the microfabricated apertures of the devices. Chips were made with surface areas of about 1 cm$^2$ and with a final thickness of roughly 0.5 mm. Circular apertures of 25 $\mu$m through 250 $\mu$m (diameter) were plasma etched in 500 nm thick silicon nitride. The chips were covered in a thick polyimide, except for a square region of exposed silicon nitride 500 $\mu$m on a side.

Fabrication was done at the Stanford Nanofabrication Facility (SNF) with 4 inch, <100> orientation, boron-doped, double-polished silicon wafers, nominally 500 $\mu$m thick. Using low-pressure chemical vapor deposition (LPCVD), a thin layer (500 nm) of silicon nitride was grown on the surface of the wafers. Standard contact photolithography and plasma etching of the silicon nitride was used to define the small features (e.g., the apertures). The larger features on the backside of the wafer were similarly defined using backside alignment, contact photolithography, and plasma etching.

The silicon was etched anisotropically along the {111} plane at an angle of 54.7° to the wafer surface. The square hole in the backside of the wafer was chosen to yield a square 180 $\mu$m larger than, and centered on, the aperture. This left a thin silicon nitride membrane freely spanning the region without any silicon support. Because of the high tensile strength of silicon nitride, this nitride membrane was quite strong and stable, and was able to readily withstand the forces generated during processing.

With the features defined in the silicon nitride, the wafers were placed in 20% tetramethylammonium hydroxide (TMAH) at 100° C. for approximately 6 hours. The silicon nitride acted as a mask, allowing the TMAH to etch anisotropically through the wafer along the {111} crystal plane.

Since the exposed silicon is conductive, it was necessary to oxidize the surface to reduce capacitance and noise. This was accomplished with a steam oxidation at 1100° C. for 4 hours, providing ~1.1 $\mu$m of oxide. Finally, to reduce the capacitance further, a photosensitive polyimide (Durimide 7520, Arch Chemicals, Zwijndrecht, Belgium) was spun on 30–70 $\mu$m thick, exposed under a contact aligner, developed, and cured, yielding a coating 15–35 $\mu$m thick.

To create a hydrophobic surface, the chips were then soaked in a mixture of hexadecane (Sigma, St. Louis, Mo.), chloroform, and octyltrichlorosilane (Aldrich, Milwaukee, Wis.) in a ratio 80:19:1 (by volume) for 15 minutes per side. Two rinses in chloroform for 5 minutes each completed the processing. The coating was tested by applying ~5 $\mu$l droplets of water and verifying that the contact angle was greater than 90°.

One advantage of silicon is the ability to control the thickness of the bilayer supporting partition (BSP). The thickness of the silicon nitride BSP was chosen to be an order of magnitude smaller than TEFLON® (Polytetrafluoroethylene—PTFE) partitions used to form apertures for bilayer formation (6–25 $\mu$m), with the expectation that thinner partitions provide a smaller solvent torus and a larger bilayer area. The partition is still a couple of orders of magnitude larger than a 2–4 nm bilayer, so bending of the lipids from the edges of the partition to the bilayer is still necessary. However, this bending distance is smaller, yielding a larger bilayer area relative to the aperture size. The impact of this upon stability is unknown, but it does allow more area for protein insertion and the ability to create bilayers across smaller apertures.

An ASC is to able to provide precise stimulation of neurons and the making of sensitive electrical measurements. As with any electronic circuit, excessive capacitance may present a problem by increasing electrical noise. Excessive capacitance is a problem for two reasons: (1) electrical noise due to the access resistance in series with this capacitance, and (2), where a lipid bilayer is to be made across the aperture of an ASC, the inability to observe the membrane capacitance over the background. Since silicon is a conductor at room temperature, any contact of the bath to the silicon effectively connects the entire area of the chip to the system. A 1 cm$^2$ chip with 500 nm of silicon nitride ($\epsilon \approx 7.5$) has a capacitance of 13 nF, three orders of magnitude greater than the capacitance of a 25 $\mu$m diameter bilayer.

However, a thin BSP in a solution containing charge-carriers has a large capacitance, which may present a problem where precise electrical measurements or precise electrical stimulation of a cell are desired. The solution to this problem was found to be two-fold. First, to remove the electrical connection between the silicon and bath, the wafers were exposed to steam at 1100° C., yielding just over a micron of oxide on all exposed silicon surfaces. This reduced the capacitance by a factor of two, since the system effectively becomes two nitride capacitors in series connected by a silicon conductor. It does, however, simplify the capacitative model of the system by removing discontinuities that would occur as the bath contacts the silicon.

Second, capacitance was reduced by addition of a polyimide layer. A negative, photosensitive polyimide ($\epsilon$=3.5) was chosen that can be processed using standard lithography. An application of 30 to 100 $\mu$m of polyimide becomes 15 to 50 $\mu$m when cured. In addition, the cured polyimide is highly resistant to solvent degradation. The design leaves 500 $\mu$m by 500 $\mu$m of nitride uncovered over the aperture. Manipulation of the solution level so that only 5 mm by 5 mm of the chip was exposed to solution, reducing the capacitance from 35 $\mu$m of polyimide to only 22 pF.

EXAMPLE 3

Bilayer Formation Across Silicon Nitride Apertures

Lipid bilayers were formed by the method of Montal and Mueller (1972). In practicing the Langmuir-Blodgett technique, one raises two lipid monolayers across an aperture, allowing the lipids to align their hydrophobic tail portions across the aperture so as to form a lipid bilayer. Because of the hydrophobic nature of the lipid tails, in order to form stable bilayers the surface of a BSP must also be hydrophobic. If the substrate is hydrophobic, the lipids can smoothly transition from coating the substrate to spanning the aperture. To reverse the wetting properties of the naturally hydrophilic silicon nitride, the silicon nitride was coated with an alkylsilane (octyltrichlorosilane). Application of this coating was quite simple and very effective. It was not found to be possible to form a bilayer with untreated devices. Use of longer carbon chain silanes or alternative materials to make the surface even more hydrophobic would further increase bilayer stability.

The characteristics of the devices are shown in Table 1. The thickness of the polyimide was varied to verify our background capacitance model for the chips. The model is based upon our chambers, where the baths contact 5 mm by 5 mm of chip. The intrinsic capacitance of the baths and amplifier was measured to be 7.2 pF, and is included in this number. For a 50 $\mu$m aperture device, where the polyimide is 32 um thick, the model yields a background capacitance of 45 pF, compared to 77 pF for 6 $\mu$m thick Teflon®.

TABLE 1

Characteristics of the devices used in this study. The polyimide thickness and total capacitance are measured, while the other properties are calculated.

| Aperture Size ($\mu$m) | Polyimide Thickness ($\mu$m) | Chip Background Capacitance (pF) | Total Capacitance (pF) | Bilayer Capacitance ($\mu$F/cm$^2$) | Expected Noise (pA) |
|---|---|---|---|---|---|
| 25 | 9.6 | 100.1 | 103.4 +/− 1.8 (n = 6) | 0.67 +/− 0.36 | 3.4 |
| 50 | 32.1 | 45.0 | 57.7 +/− 2.1 (n = 10) | 0.65 +/− 0.11 | 1.4 |
| 75 | 19.8 | 60.6 | 91.1 +/− 2.0 (n = 9) | 0.69 +/− 0.04 | 1.8 |
| 100 | 17.5 | 66.4 | 117.4 +/− 1.1 (n = 2) | 0.65 +/− 0.01 | 2.0 |
| 150 | 21.7 | 59.4 | 182.6 +/− 5.3 (n = 6) | 0.70 +/− 0.03 | 2.6 |
| 250 | 19.6 | 65.9 | 379.8 +/− 6.3 (n = 5) | 0.64 +/− 0.01 | 4.4 |

The bilayer specific capacitance was determined simply by dividing the difference between the measured total capacitance and the calculated background capacitance by the area of the aperture. This number is in the range of 0.64 to 0.70 $\mu$F/cm$^2$ and corresponds well with that found in other artificial bilayer experiments. The total capacitance was measured within a few minutes after bilayer formation to avoid changes due to bilayer thinning. Note that as the aperture area decreased, the bilayer capacitance became quite small compared to the background, yielding a large error in the specific capacitance.

The empirical evidence for the formation of a bilayer on any chip was threefold. For the largest size apertures, the change in capacitance due to the bilayer was readily observable. For a typical specific capacitance value of 0.65 $\mu$F/cm$^2$, a bilayer on a 100 $\mu$m aperture would have a capacitance of 51 pF, which is easily observed over a 65 pF background. In addition, a resistance through the aperture greater than 1 G$\Omega$ indicates the presence of a bilayer. For all aperture sizes, a "gigaseal" of at least 2.5 G$\Omega$ was observed, indicating the formation of a bilayer.

For smaller apertures, it was more difficult to observe the capacitance change over the background. In this case, membrane-bound proteins that affect the electrical properties of the bilayer, such as carriers and ion channels, offered the best proof of the formation of a bilayer. The ion channel peptide Gramicidin D (gD), was chosen for ease of use and large conductance change. A lipid bilayer membrane is required in order for Gramicidin D to increase current flow. After adding 5 to 20 µl of 2 mg/ml gD (Sigma, St. Louis, Mo.) in ethanol to each bath, the conductance of the bilayer dramatically increased within minutes, while the capacitance remained constant. The addition of ethanol by itself had no effect. Thus, the increase in current flow in response to an applied potential (measured by an increase in conductance) indicated that a true lipid bilayer had been formed.

Observing individual ion channels or pores requires that the electrical noise to be as small as possible. In addition to environmental sources and capacitative noise, there are two major sources of electrical noise: photocarriers in the silicon, and access resistance. The first noise source, light, is produced when light incident upon the chip excites carriers across the band gap, creating a fluctuating charge between the two layers of nitride. Depending on the source and intensity of light, the noise produced may measure tens to hundreds of picoamperes peak-to-peak. Simply shutting off room lights or enclosing the setup in a light proof box was sufficient to reduce the electrical noise contributed by from noise source.

The other source of electrical noise was due to the access resistance of the baths in series with the bilayer capacitance. The total access resistance ($R_a$) contains three components: the bulk bath resistivity (32 A-cm), the bath resistivity in the aperture, and the access resistance to the aperture. For a small access resistance, the expected noise in amperes rms was $\sqrt{4kTR_\alpha(2\pi f^2 C)^2}$ where f is the measurement bandwidth.

The results of this calculation for each tested chip are shown in Table 1. For the 50 µm aperture, the expectation from this calculation was 1.4 pA rms, while the actual measured values were between 1.8 pA and 2.4 pA. The difference was attributed to local environmental noise.

EXAMPLE 4

Bilayer Stability and Lifetime

Bilayers were formed by the technique of Montal and Mueller (1972). The aperture was first pretreated with ~5 µl of 1:9 (v:v) hexadecane:hexane (Burdick & Jackson, Muskegon, Mich.). The chip was mounted between two Teflon® baths with silicone high vacuum grease (Dow Corning, Midland, Mich.). Each bath was filled with 1 M KCl to just below the aperture. A solution of 5 µl at 10 mg/ml of 1,2-diphytanoyl-sn-glycerophosphocholine (Avanti Polar Lipids, Alabaster, Ala.) in chloroform was applied to each bath and allowed to evaporate. When the water level in each bath was raised, a lipid bilayer formed across the aperture, as evidenced by the capacitance and conductance of the device.

The ability to support the formation of a bilayer that will be stable for an extended period of time is an important property for any supporting substrate. Lipid bilayer membranes formed on ASCs were found to be very stable. ASCs were found to have two advantages over TEFLON® (Polytetrafluoroethylene—PTFE) partitions in terms of stability. First, lipid bilayer membranes formed on ASCs were thinner than those formed on TEFLON® (Polytetrafluoroethylene—PTFE) partitions, but are also more rigid. TEFLON® (Polytetrafluoroethylene—PTFE) partitions flex under changes in pressure, whereas nitride is comparatively inflexible. Second, the nitride surface and aperture edge are smooth at the nanometer level (see FIG. 2), unlike mechanically formed apertures in TEFLON® (Polytetrafluoroethylene—PTFE) partitions, which have micron-scale defects along the aperture edge.

Membrane stability was demonstrated by observing lipid bilayer membrane lifetime. Roughly half of the bilayers broke within the first few minutes, but some were stable for much longer. The longest bilayer lifetime observed was 8 hours. No attempts to measure systematically for longer than this time scale were made. It was found that the number of stable bilayers that were formed depended heavily on the cleanliness of the chip. It was rather easy to form a stable bilayer membrane using a fresh ASC device that had just completed processing. However, it was more difficult to form a stable bilayer membrane on an ASC that was reused after cleaning. Lipid bilayer membrane formation was found to be impossible following use of a cleaning process that left a residue across the aperture.

EXAMPLE 5

Single-Channel Recordings with α-hemolysin

Ion channel activity due to staphylococcal α-hemolysin (αHL) channels was studied in lipid bilayer membranes formed across ASC apertures. This 293-amino acid heptameric pore forms 2 nm channels through the lipid bilayer. Single-channel recordings were performed with a patch clamp amplifier (Heka EPC-8, Heka Elektronik, Lambrecht, Germany) and an analog-to-digital converter (Instrutech ITC-18, Port Washington, N.Y.) sampled at 10 kHz. Filtering was performed with a built-in 7-pole low-pass Bessel filter at 5 kHz. The data was collected on computer using Pulse 8.4 (Heka) and analyzed with Igor Pro 4.0 (WaveMetrics, Lake Oswego, Oreg.). The αHL pores were added to the cis chamber (1 to 10 µl at 321 ng/ml), and held at −40 mV (trans side grounded). Addition of αHL to the trans side also yielded channels, but the diffusion time was longer due to the relatively long, narrow cavity.

Figure 6A:
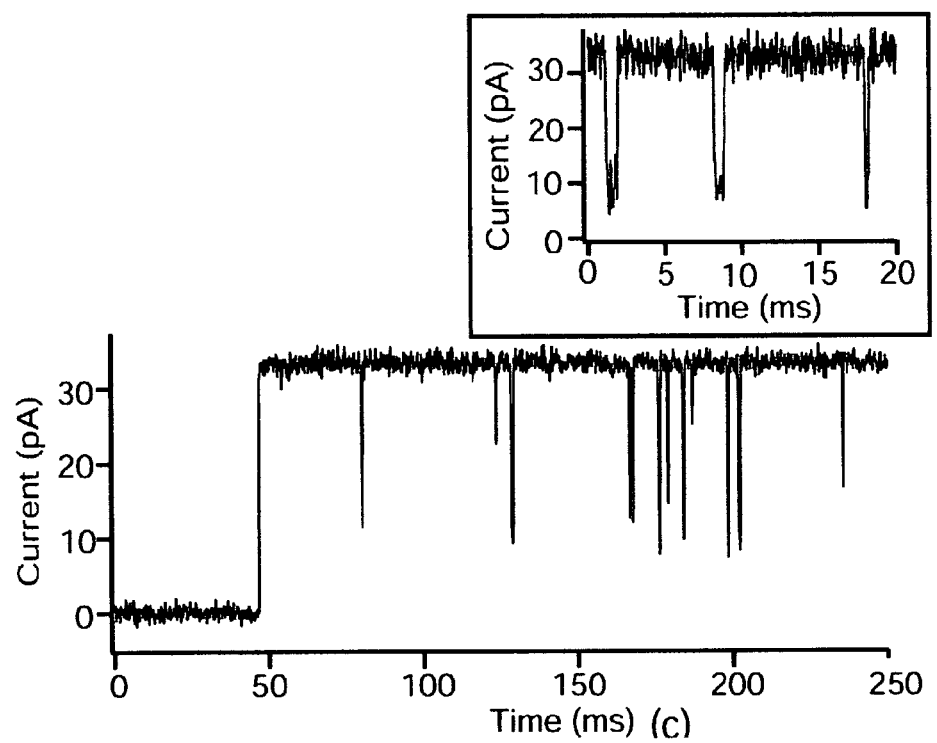
FIG. 6A shows current flow through α-hemolysin channels in an artificial bilayer membrane formed across a nanoaperture of an artificial synapse chip embodying features of the invention, with current shown along the vertical axis and time along the horizontal axis, the insert showing a short portion of the record at expanded scale along the time axis.
Figure 6B:
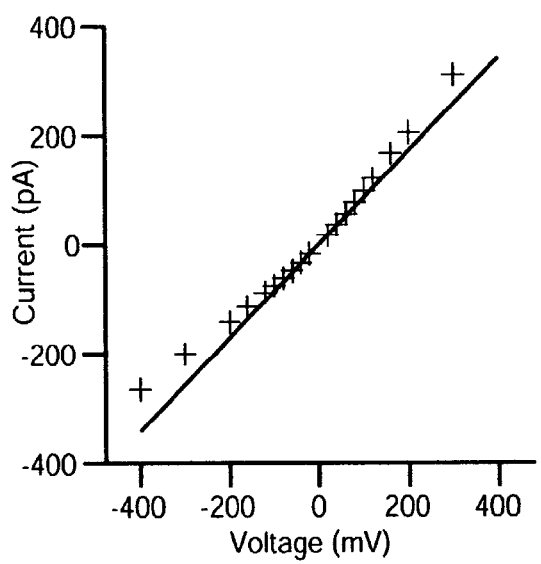
FIG. 6B is a plot of the measured current flow through α-hemolysin channels in an artificial bilayer membrane formed across a nanoaperture of an artificial synapse chip embodying features of the invention, with current shown along the vertical axis and time along the horizontal axis.
Figure 6C:
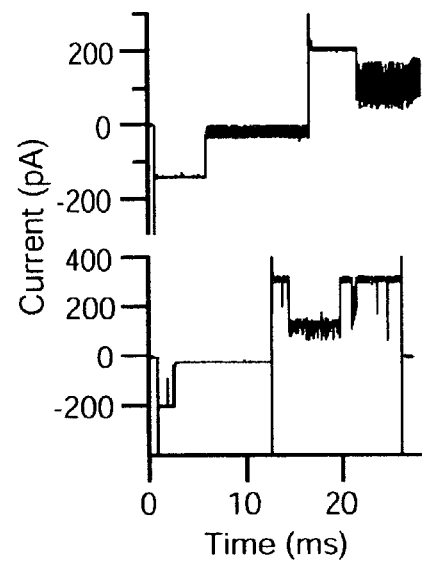
FIG. 6C shows current flow through two α-hemolysin channels in an artificial bilayer membrane formed across a nanoaperture of an artificial synapse chip embodying features of the invention, with current shown along the vertical axis and time along the horizontal axis.

FIGS. 6A and 6C illustrate α-hemolysin (αHL) single-channel currents recorded from artificial bilayer membranes across 100 µm apertures in microfabricated devices exposed to β-cyclodextrin (ACD) in the trans bath. The holding potential was +40 mV (the cis bath was at ground potential). Shown in FIG. 6A are representative single-channel data for αHL channels. In similar experiments, voltage pulses of −40 mV were applied for 750 ms, and currents were recorded, giving measured currents of 31.0 +/−3.2 pA per channel). The calculated pore conductance of 811 +/−55 pS was typical for αHL channels. The added β-cyclodextrin (βCD), which inserts reversibly in the trans side of the channel, causes fluctuations in the current flow through the channel as the molecules move in and out of the protein. This effect is found at micromolar concentrations (e.g., 40 µM to 300 µM of βCD). When a channel becomes blocked, a clearly observable current reduction occurs, as shown in FIG. 6A. Partial blocking events from βCD appear as downward spikes. The βCD events are more clearly shown in the inset at higher sampling rates (100 kHz) and expanded time scales. These results were in agreement with previous results for such channel recordings obtained with bilayers formed across TEFLON® (Polytetrafluoroethylene—PTFE) partitions. FIG. 6B shows a current voltage plot of αHL single-channel currents in 1M KCl, 10 mM Kpi at pH 7.4. The fit (solid line) is through the points at −40 mV and +40 mV. FIG. 6C shows current as a function of time for two aHL channels in artificial bilayer membranes across 100 µm apertures in microfabricated devices at +/−200 mV and at +/−300 mV.

EXAMPLE 6

Use of the Artificial Synapse for Single Cell Stimulation and Excitation

Methods for stimulating cells through the nanoaperture and measuring their activity using fluorescence from $Ca^{2+}$ sensitive dyes include the following: (1) voltage clamping the cell to the aperture (applying suction via the microchannel) and varying the voltage of the buffer in the microfluidic channel; (2) chemical stimulation of the cell by pulsing a bolus of neurotransmitter to the under side of the cell; (3) microfluidic bolus of liposomes containing transmitters to the aperture opening; (4) microfluidic reservoir of engineered cells that would stimulate the neurite through the release of transmitters.

A subconfluent layer of PC12 cells is cultured on an array of microapertures fabricated. Cell activity is measured by fluorescence microscopy with the cells loaded with $Ca^{2+}$ sensitive dyes (such as, e.g., Indo-1, fura −2, fluo- 3, calcium green, aequorin). The fluorescence serves both to monitor the activity of the cell directly above the aperture and to see the effect on neighboring cells. The surface may be modified around the aperture to achieve a good "seal" to the cell membrane (where a good seal is mechanically stable and has an electrical resistance near to or in excess of one gigaΩ). Surface modifiers may include different extracellular matrix proteins and "cell Tak" (Becton Dickinson). Different stimulation techniques suitable for use with the devices and methods of the invention include temporal and spatial resolution and chronic stimulation. The size of the aperture may be varied as well. In addition, the aperture may be coated with a single lipid bilayer with preloaded ion channels or artificial pore-forming molecules, including proteins that can form pores. These lipid bilayer membranes can be formed by as described in previous Examples. The ion channel or pore-forming molecules may be are already part of the membrane if they were part of the material used to form the membrane, or are then incorporated into the bilayer.

A microstamp, such as a PDMS stamp, is used to make a micropattern to overlay onto an array of microfabricated apertures. The micropattern is effective to direct the growth of cells cultured on the ASC substrate so that neurites of the cells grow to, adjacent to, or over ASC apertures. Any suitable alignment system may be used to align the microstamp pattern with the apertures on the chip. PC12 cells, retinal ganglion cells, or other cells grown on the substrate may be stimulated as described above on the array of microapertures connected the various microfluidics reservoirs.

Cells growing on ASC substrates are stimulated by voltage pulses from electrodes in contact with the solution in the recess and in the reservoir. The voltage pulses are effective to depolarize the cell process adjacent or across the aperture. Depolarization voltages range from about 1 mV to about 100 mV. Depolarizations of between about 10 mV to about 50 mV are found to be the most effective.

Liposomes containing the neurotransmitter acetylcholine and adenosine-tris-phosphate are placed in the reservoir. A lipid bilayer membrane spans the aperture. Cells with processes growing across or adjacent to the aperture are stimulated by contact with neurotransmitter released by liposomes fusing with the lipid bilayer membrane. Fusion is promoted by an osmotic gradient across the liposome membrane and across the lipid bilayer membrane. Fusion is also promoted by electrical gradients, optical methods, inclusion of fusion-promoting molecules in the liposomes and or membranes, and in other ways.

Neuronal excitation is measured using fluorescence with $Ca^{2+}$ sensitive dyes, electrical recording, and biochemical analysis to detect neurotransmitter release from the cultured cells into solutions in the recess or reservoir adjacent the aperture.

EXAMPLE 7

Stimulation of Cells on an Artificial Synapse Chip

Figure 7A:
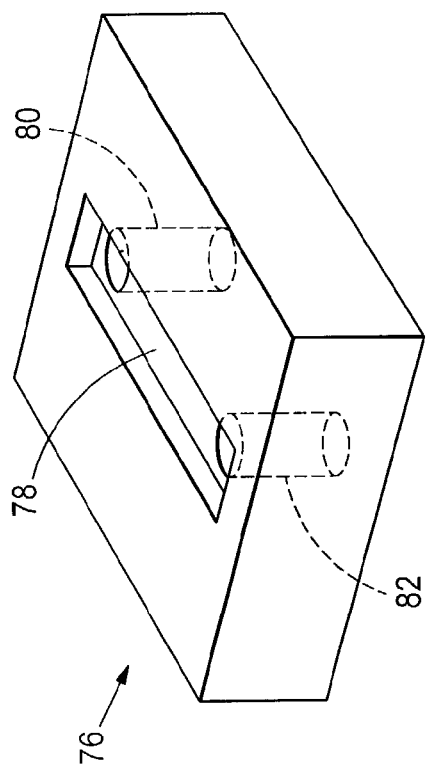
FIG. 7A is a schematic perspective view of a fluidic channel portion of a device embodying features of the invention.
Figure 7B:
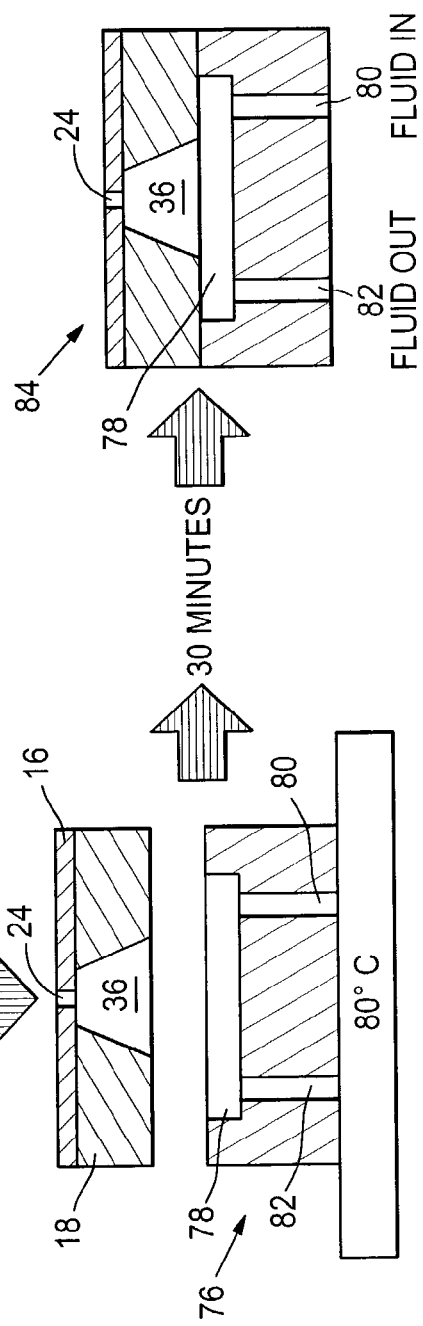
FIG. 7B is a schematic representation of the bonding together of a fluidic channel portion with a silicon aperture portion of a device embodying features of the invention, showing a combined device in cross-section.

A device for localized fluid delivery 84 consists of two components, one for localization and one for fluid manipulation. Devices as illustrated in FIGS. 1A–1D, with or without a substrate 12 or base layer 20, combined with the device of FIG. 7A, as shown in FIG. 7B, are configured for localized fluid delivery. FIG. 7A illustrates a fluidic channel portion 76 embodying features of the invention, configured to provide fluid flow to and from a reservoir 36 and aperture 24 of an ASC 10. A device for localized fluid delivery 84 is illustrated in FIG. 7B. FIG. 7B illustrates the bonding process between an ASC 10 and a device for fluid manipulation 76 to provide a device for localized fluid delivery 84. For localization, the devices use small apertures 24 (5 or 10 µm) in thin silicon nitride membranes 16 (e.g., FIG. 7B). By providing an aperture 24 of small enough size, fluid delivery may be limited in both volume and location. The devices 84 used in these experiments were 1 cm² chips, with a thickness of roughly 0.5 mm. The silicon nitride layer 16 was patterned using plasma etching to create the aperture 24 and a square hole (a reservoir 36) in the backside of the wafer. The silicon was etched anisotropically along the (111) plane at an angle of 54.7° to the wafer surface, using the silicon nitride as an etch mask. The square hole 36 in the backside of the wafer was chosen to yield a region 100 µm larger than the aperture 24. This left a thin silicon nitride membrane 16 freely spanning the region without any silicon support. Silicon nitride is transparent to the visible wavelengths of light, so cells were easily imaged through this membrane. Because of the high tensile strength of silicon nitride, this silicon nitride membrane was quite strong and stable; it readily withstood the forces generated during processing.

After localization, the other necessary component for a device for localized fluid delivery 84 is fluid delivery to the aperture. To accomplish this, a channel 78 made from PDMS (FIG. 7A), in fluid continuity with an inlet 80 and an outlet 82, was attached beneath the aperture 24 of an ASC 10 (FIG. 7B). A master mold was made from 300 µm thick SU-8 photoresist on a silicon wafer using conventional photolithography and a mask made on a transparency using an office printer. The channels 78 were 900 µm wide, 150 µm deep, and 8 mm long, while the PDMS was poured approximately 5 mm deep. A cartoon depicting this design is shown in FIG. 7A.

Once the PDMS cured, the channels 78 were attached to the ASC 10 as illustrated in FIG. 7B. The PDMS was diced into 1 cm² pieces, with one channel per device. Both the silicon and the PDMS were cleaned in a dilute hydrochloric acid solution (1:4), followed by air plasma at 100 W for 60 seconds. The ACS 10 with its silicon aperture 24 was aligned and centered on top of the PDMS channel 78, and bonded by squeezing the pieces together (~0.2 N) and heating on a hot plate at 80° C. (see FIG. 7B). Once complete, this bond was irreversible; the PDMS will tear before separating from the silicon nitride.

Since rat pheochromocytoma cells (PC12) do not readily adhere to most substrates, including silicon/silicon nitride, it was therefore necessary to treat the devices 84 to modify its surface before seeding with cells. The devices 84 were first immersed in poly(D-lysine) at 50 $\mu$g/ml for 30 minutes at room temperature. The poly(D-lysine) provides a sticking layer for an application of mouse laminin, to which the PC12 cells adhered and spread. After rinsing the devices 84 in phosphate-buffered saline (PBS), the laminin was applied at 5 $\mu$g/ml in PBS for 8 hours in an incubator (37° C., 6.5% $CO_2$). The devices 84 were then rinsed in PBS and were ready for use.

Measurement of bradykinin stimulation was accomplished by observing changes in intracellular $Ca^{2+}$ levels using fluo-4 (Molecular Probes, Eugene, Oreg.). The loading solution was made from fluo-4 reconstituted in dimethylsulfoxide (DMSO) at 1 mM mixed in Ringer's solution (135 mM NaCl, 5 mM KCl, 10 mM D-glucose, 2 mM $MgCl_2$, 2 mM $CaCl_2$, 10 mM HEPES, pH 7.2) to a final fluo-4 concentration of 1 $\mu$M.

The stimulating solution was a mixture of bradykinin (Sigma, St. Louis, Mo.), Ringer's, and sulforhodamine 101 (Sigma). Bradykinin was reconstituted in Ringer's at 1 mg/ml (1 mM), and then diluted to the desired testing concentration. Sulforhodamine (Texas Red) was reconstituted in DMSO at 8 mM, and added to the stimulating solution to yield a final concentration of 4–8 $\mu$M. The Texas Red dye provided a means to visualize simultaneously the fluid flow and stimulation.

Changes in fluorescent levels were observed with either an inverted fluorescence microscope or an upright confocal microscope. The inverted microscope, used for the single-cell stimulation data was a Nikon TE300 (10x, 0.30 numerical aperture (NA)) with a Hamamatsu Orca ER CCD camera. The data was collected with Metamorph (Universal Imaging Corporation, Downingtown Pa.). The confocal microscope, used for the multi-cell and two-color experiments, was a Nikon E800 (10 x dipping objective, 0.30 NA) with a Nikon PCM 2000 confocal unit. Two lasers were used simultaneously to excite the fluo-4 (Argon ion, 488 nm) and Texas Red (HeNe, 543 nm). Images were sampled with two photomultiplier tubes simultaneously (515/30 bandpass and 605/32 bandpass filters), and analyzed using SimplePCl (Compix Inc., Cranberry Township, Pa.).

The microfluidic system, including devices 84 and associated fluid supply and syringes, supplied a small amount of stimulant through the aperture. The experimental design was to flow bradykinin through the channel 78 and to allow passage of bradykinin through the aperture 24. While there are multiple methods for moving fluids in microchannels, and causing fluid to flow within a fluid delivery channel, including inducing flow by pumps, gravity, pressure (such as pressure produced by a piston moving within a cylinder), electroosmotic and other means, we chose a pressure-driven flow using a syringe. The bradykinin flow through the aperture 24 was due to a combination of the pressure gradient created by the syringe and chemical diffusion.

The fluid was supplied by inserting 24-gauge Teflon hoses into each access hole 80 and 82. One-milliliter tuberculin syringes were used to drive the fluid through the hoses, at a rate of 10 to 30 $\mu$l/s. Injected volumes range from 250 $\mu$l through 1000 $\mu$l, taking 15 to 60 seconds to deliver. The average flow rate was 16 $\mu$l/s; when combined with the channel geometry, this yielded a Reynolds number of approximately 3100, above the limit for laminar flow. Being above the laminar limit is an advantage in this system. There is a 500 $\mu$m gap between the channel 78 and the aperture 24 due to the wafer thickness. Nonlaminar flow allows mixing to occur by methods other than diffusion, speeding the rate at which bradykinin reached the aperture.

With the fluidic delivery system in place, cell stimulation was accomplished by delivering an appropriate amount of stimulant to the cells growing on the supporting layer 16. Rat pheochromocytoma cells (PC12) were chosen because of their usefulness as a neurobiological model, and because of the ease of their care and their ready availability. The PC12cell line changes its intracellular $Ca^{2+}$ levels upon stimulation by bradykinin, achieving a maximum change at an external bradykinin concentration of 1 $\mu$M. The cells were seeded on the devices 84 at least four hours before testing to allow them to adhere.

Two parameters of control over stimulation radius were concentration and volume. By adjusting either the concentration or the volume of bradykinin supplied, the distance from the aperture at which cells were stimulated was controlled. When a large total quantity of bradykinin was delivered to the aperture 24 (high concentration or large volume), many PC12 cells were stimulated. This is shown in FIGS. 8A–8C, where time-lapse confocal micrographs of multi-cell stimulation show a wave of stimulated PC12 cells as bradykinin flows past PC12 cells adherent to the surface of a device 84. The aperture 24 was 10 $\mu$m in diameter (half the size of a PC12 cell body) and is shown located at the center of the dotted circles in FIGS. 8A–8C.

As shown in FIGS. 8A–8C, bradykinin (100 $\mu$M) was driven through the channel 78 for approximately 21 seconds. Intensity cross-sections (arbitrary units, constant scale) indicate which PC12 cells were stimulated. FIG. 8A illustrates the control situation before application of bradykinin to the PC12 cells. The intensity plot in FIG. 8A shows two cross-sections at time zero, indicating that, at the starting time, no cells were stimulated. A Ringer's solution containing 100 $\mu$M bradykinin was applied to the channel 78 just after the frame displayed in FIG. 8A was taken. As the fluid radiated outward from the aperture 24, PC12 cells were stimulated. Within 3 seconds, a PC12 cell 25 $\mu$m from the aperture was stimulated, as the bright cell to the left and below the aperture 24 in FIG. 8B shows (FIG. 8B, arrow). After another 6 seconds, 9 seconds after the bradykinin began to flow, cells further away (100 $\mu$m) from the aperture 24 were stimulated (FIG. 8C, dual arrows). Other PC12 cells in the region were also stimulated; the arrows indicate only representative events for which the intensity is displayed.

This example demonstrates the ability to stimulate cells locally using a chemical stimulus, providing a neurobiological system configured to stimulate cells with physiological stimuli and configured for use at desired location within an organ or tissue of animal. By varying the amount and concentration of neurotransmitter supplied through a microaperture, the stimulation distance and timing can be controlled, providing control compatible with normal animal physiological.

EXAMPLE 8

Implantation of an Artificial Synapse Chip

An artificial synapse chip is implanted into the subretinal space in the retina of a rabbit. A New Zealand white rabbit is anesthetized according to standard animal surgery techniques. An incision is made in the sclera near to the equator of the eye and a small scleral flap opened to provide access to the underlying choroid and retina. An incision is gently made in the choroid, choriocappilaris, Bruch's membrane and across the retinal pigment epithelium layer to provide access to the subretinal space facing the photoreceptors. Saline is gently infused into the subretinal space to separate the retinal pigment epithelium and the retinal photoreceptors. An ASC is placed into the subretinal space and slowly advanced towards the fovea from the point to entry near the equator of the eye. After the ASC is located at the desired location near to the fovea, a needle is inserted through the opening in the sclera, into the vitreous, and a small air bubble is injected into the vitreous to provide pressure against the retina to hold the retina in place over the implant. The incision is then closed. The air bubble shrinks and disappears within a few days as the gas is absorbed.

It will be apparent from the foregoing that, while particular forms of the invention have been illustrated and described herein primarily in terms of an artificial synapse chip, a device for localized fluid delivery, and similar devices and systems, various modifications can be made without departing from the spirit and scope of the invention. Moreover, those skilled in the art will recognize that features shown in one embodiment may be utilized in other embodiments. Terms such a "device", "portion", "section", "steps" and words of similar import when used herein shall not be construed as invoking the provisions of 35 U.S.C. §112(6) unless the following claims expressly use the terms "means" or "step" followed by a particular function without specific structure or action.

While particular forms of the invention have been illustrated and described, it should be apparent that various modifications can be made without departing from the spirit and scope of the invention. Accordingly, it is not intended that the invention be limited, except as by the appended claims.

What is claimed is:

1. An ocular implant, comprising:
   (a) a substrate having a surface biocompatible with at least a portion of a cell, said surface having a micropattern to direct the growth of a cell process of said cell;
   (b) an aperture in said surface, said aperture capable of receiving said cell process; and
   (c) a reservoir containing a fluid connected to said aperture, said aperture providing a conduit for delivery of said fluid from said reservoir to said cell process in said aperture,
   wherein said ocular implant is oxidized and coated with a polyimide layer to reduce capacitance.

2. The ocular implant as set forth in claim 1, wherein said micropattern comprises chemoattractant factors.

3. The ocular implant as set forth in claim 1, wherein said fluid comprises neuromodulatory agents.

4. The ocular implant as set forth in claim 3, wherein said neuromodulatory agent are neurotransmitters.

5. The ocular implant as set forth in claim 1, further comprising an electrical circuit, having at least one contact effective to stimulate at least a portion of said cell process.

6. The ocular implant as set forth in claim 5, wherein said cell process stimulation is selected from the group consisting of stimulation of a neurite, stimulation of a cell through a neurite, and direct stimulation of a cell.

7. The ocular implant as set forth in claim 1, wherein said ocular implant is implanted adjacent to the inner limiting membrane or in the subretinal space.

8. The ocular implant as set forth in claim 1, further comprising a microfluidic device in operable relationship with said fluid in said reservoir.

9. The ocular implant as set forth in claim 8, wherein said microfluidic device is a mechanical device.

10. The ocular implant as set forth in claim 8, wherein said microfluidic device is a micro-electro-mechanical device.

* * * * *